United States Patent
Yersin et al.

(10) Patent No.: US 9,537,117 B2
(45) Date of Patent: Jan. 3, 2017

(54) SINGLET HARVESTING WITH DUAL-CORE COPPER (I) COMPLEXES FOR OPTOELECTRONIC DEVICES

(75) Inventors: Hartmut Yersin, Sinzing (DE); Uwe Monkowius, Linz (AT); Thomas Hofbeck, Freystadt (DE)

(73) Assignee: CYNORA GMBH, Bruchsal (DE)

( * ) Notice: Subject to any disclaimer, the term of this patent is extended or adjusted under 35 U.S.C. 154(b) by 473 days.

(21) Appl. No.: 14/236,202

(22) PCT Filed: Aug. 2, 2012

(86) PCT No.: PCT/EP2012/065203
§ 371 (c)(1),
(2), (4) Date: Jan. 30, 2014

(87) PCT Pub. No.: WO2013/017675
PCT Pub. Date: Feb. 7, 2013

(65) Prior Publication Data
US 2014/0167027 A1    Jun. 19, 2014

(30) Foreign Application Priority Data

Aug. 2, 2011  (DE) .................... 10 2011 080 240
Mar. 29, 2012  (EP) ......................... 12162191

(51) Int. Cl.
*B32B 9/00* (2006.01)
*H01L 51/56* (2006.01)
(Continued)

(52) U.S. Cl.
CPC ............... *H01L 51/56* (2013.01); *C07F 9/587* (2013.01); *C09K 11/06* (2013.01); *H01L 51/009* (2013.01);
(Continued)

(58) Field of Classification Search
USPC ............................................. 428/690; 257/40
See application file for complete search history.

(56) References Cited

U.S. PATENT DOCUMENTS

| 8,618,317 B2* | 12/2013 | Stoessel ................. | C09K 11/06 252/301.16 |
| 2007/0072001 A1* | 3/2007 | Tsuboyama ............ | C09K 11/06 428/690 |

(Continued)

FOREIGN PATENT DOCUMENTS

| DE | 102009030475 A1 | 1/2011 |
| JP | 2005190987 A | 7/2005 |

(Continued)

OTHER PUBLICATIONS

H. Yersin, "Triplet Emitters for OLED Applications Mechanisms of Exciton Trapping and Control of Emission Properties," Topics in Current Chemistry, 2004, pp. 1-26, vol. 241, No. 1.
(Continued)

*Primary Examiner* — Austin Murata
(74) *Attorney, Agent, or Firm* — Ryan, Mason & Lewis, LLP

(57) ABSTRACT

The invention relates to dimeric copper(I) complexes according to formula A, in particular as emitters in optoelectronic devices such as organic light emitting diodes (OLEDs) and other devices
(Continued)

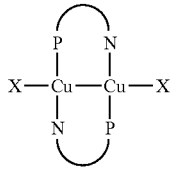

Formula A wherein:
Cu: Cu(I),
X: Cl, Br, I, SCN, CN, and/or alkynyl and
P∩N: a phosphine ligand substituted with a N-heterocycle.

20 Claims, 18 Drawing Sheets

(51) Int. Cl.
| C07F 9/58 | (2006.01) |
| C09K 11/06 | (2006.01) |
| H01L 51/00 | (2006.01) |
| H01L 51/50 | (2006.01) |

(52) U.S. Cl.
CPC ....... H01L 51/0091 (2013.01); H01L 51/5016 (2013.01); *C09K 2211/188* (2013.01); *Y02E 10/549* (2013.01)

(56) References Cited

U.S. PATENT DOCUMENTS

| 2007/0111026 | A1 | 5/2007 | Deaton et al. | |
| 2008/0064893 | A1 | 3/2008 | Peters et al. | |
| 2009/0212280 | A1* | 8/2009 | Werner | C09K 11/06 257/40 |
| 2010/0038632 | A1* | 2/2010 | Ganeshamurugan | H01L 51/0084 257/40 |
| 2011/0108769 | A1* | 5/2011 | Yersin | C09K 11/06 252/301.16 |
| 2012/0184738 | A1* | 7/2012 | Yersin | C07F 1/005 544/225 |

FOREIGN PATENT DOCUMENTS

| WO | 2005054404 A1 | 6/2005 |
| WO | WO2010149748 A1 | 12/2010 |
| WO | 2011063083 A1 | 5/2011 |

OTHER PUBLICATIONS

H. Yersin, Highly Efficient OLEDs with Phosphorescent Materials, 2008, 457 pages, Wiley-VCH Verlad GmbH & Co. KGaA, Weinheim, Germany.
C.W. Tang et al., "Organic Electroluminescent Diodes," Applied Physics Letters, Sep. 1987, pp. 913-915, vol. 51, No. 12.
D.Tanaka et al., "Ultra High Efficiency Green Organic Light-Emitting Devices," Japanese Journal of Applied Physics, 2007, pp. L10-L12, vol. 46, No. 1.
M.A. Baldo et al., "Excitonic Singlet-Triplet Ration in a Semiconducting Organic Thin Film," Physical Review B (Condensed Matter and Materials Physics), Nov. 15, 1999, pp. 14422-14428, vol. 60 No. 20.
N.C. Giebink et al., "Quantum Efficiency Roll-Off at High Brightness in Flourescent and Phosphorescent Organic Light Emitting Diodes," Physical Review B (Condensed Matter and Materials Physics), Jun. 23, 2008, 9 pages, vol. 77, No. 23.
International Search Report and Written Opinion of International Searching Authority for PCT/EP2012/065203 dated Nov. 14, 2012.
J.C. Deaton et al., "E-Type Delayed Fluorescence of a Phosphine-Supported Cu2(u-NAr2)2 Diamond Core: Harvesting Singlet and Triplet Excitons in OLEDs," Journal of the American Society, Jun. 2010, pp. 9499-9508, vol. 132, No. 27.
S.B. Harkins et al., "Probing the Electronic Structures of [Cus(u-XR2)]n+ Diamond Cores as a Function of the Bridging X Atom (X=N or P) and Charge (n=0, 1, 2)," Journal of the American Chemical Society, Feb. 2008, pp. 3478-3485, vol. 130, No. 11.
D.M. Zink et al., "Experimental and Theoretical Study of Novel Luminescent Di-, Tri-, and Tetranuclear Copper Triazole Complexes," Journal of the American Chemical Society, Organometallics, May 2011, pp. 3274-3283, vol. 30, No. 12.
K.R. Kyle et al., "Photophysical Studies in Solution of the Tetranuclear Copper(I) Clusters Cu4I4L4 (L=Pyridine or Substituted Pyridine)1-3," Journal of the American Chemical Society, Apr. 1991, pp. 2954-2965, vol. 113, No. 8.

* cited by examiner

SINGLET HARVESTING WITH DUAL-CORE COPPER (I) COMPLEXES FOR OPTOELECTRONIC DEVICES

FIELD OF INVENTION

The present invention relates to novel dimeric copper(I) complexes and their use, in particular as emitters in optoelectronic devices such as organic light emitting diodes (OLEDs) and others.

BACKGROUND OF THE INVENTION

Currently, new processes win recognition in the field of visual display and lighting technology. It will be possible to manufacture flat displays or illuminated surfaces having a thickness of less than 0.5 mm. These are notable for many fascinating properties. For example, it will be possible to achieve illuminated surfaces in the form of wallpaper with very low energy consumption. It is also of particular interest that color visual display units will be producible with hitherto unachievable colorfastness, brightness and viewing angle independence, with low weight and with very low power consumption. It will be possible to configure the visual display units as micro-displays or large visual display units of several square meters in area in rigid form or flexibly, or else as transmission or reflection displays. In addition, it will be possible to use simple and cost-saving production processes such as screen printing or inkjet printing. This will enable very inexpensive manufacture compared to conventional flat visual display units. This new technology is based on the principle of the OLEDs, the organic light-emitting diodes. Furthermore, through the use of specific organometallic materials (molecules), many new optoelectronic applications are on the horizon, for example in the field of organic solar cells, organic field-effect transistors, organic photodiodes, etc.

Particularly for the OLED sector, it is apparent that such devices are already now of economic significance, since mass production of OLED displays for mobile phones has already started. Such OLEDs consist predominantly of organic layers, which can also be manufactured flexibly and inexpensively. Worth pointing out is that OLED components can be configured with large areas as illumination bodies, but also in small form as pixels for displays.

Compared to conventional technologies, for instance liquid-crystal displays (LCDs), plasma displays or cathode ray tubes (CRTs), OLEDs have numerous advantages, such as a low operating voltage of a few volts, a thin structure of only a few hundred nm, high-efficient self-illuminating pixels, high contrast and good resolution, and the possibility of representing all colors. In addition, in an OLED, light is produced directly upon application of electrical voltage, rather than merely being modulated.

A review of the function of OLEDs can be found, for example, in H. Yersin, Top. Curr. Chem. 2004, 241, 1 and H. Yersin, "Highly Efficient OLEDs with Phosphorescent Materials"; Wiley-VCH, Weinheim, Germany, 2008.

Since the first reports regarding OLEDs (see, for example, Tang et al., Appl. Phys. Lett. 1987, 51, 913), these devices have been developed further particularly with regard to the emitter materials used, and particular interest has been attracted in the last few years by what are called triplet emitters or by other phosphorescent emitters.

OLEDs are generally implemented in layer structures. For better understanding, FIG. 1 shows a basic structure of an OLED. Owing to the application of external voltage to a transparent indium tin oxide (ITO) anode and a thin metal cathode, the anode injects positive holes, and the cathode negative electrons. These differently charged charge carriers pass through intermediate layers, which may also consist of hole or electron blocking layers not shown here, into the emission layer. The oppositely charged charge carriers meet therein at or close to doped emitter molecules, and recombine. The emitter molecules are generally incorporated into matrix molecules or polymer matrices (in, for example, 2 to 10% by weight), the matrix materials being selected so as also to enable hole and electron transport. The recombination gives rise to excitons (=excited states), which transfer their excess energy to the respective electroluminescent compound. This electroluminescent compound can then be converted to a particular electronic excited state, which is then converted very substantially and with substantial avoidance of radiationless deactivation processes to the corresponding ground state by emission of light.

With a few exceptions, the electronic excited state, which can also be formed by energy transfer from a suitable precursor exciton, is either a singlet or triplet state, consisting of three sub-states. Since the two states are generally occupied in a ratio of 1:3 on the basis of spin statistics, the result is that the emission from the singlet state, which is referred to as fluorescence, leads to maximum emission of only 25% of the excitons produced. In contrast, triplet emission, which is referred to as phosphorescence, exploits and converts all excitons and emits them as light (triplet harvesting) such that the internal quantum yield in this case can reach the value of 100%, provided that the additionally excited singlet state, which is above the triplet state in terms of energy, relaxes fully to the triplet state (intersystem crossing, ISC), and radiationless competing processes remain insignificant. Thus, triplet emitters, according to the current state of the art, are more efficient electroluminophores and are better suitable for ensuring a high light yield in an organic light-emitting diode.

The triplet emitters suitable for triplet harvesting transition metal complexes are generally used in which the metal is selected from the third period of the transition metals. This predominantly involves very expensive noble metals such as iridium, platinum and also gold (see also H. Yersin, Top. Curr. Chem. 2004, 241, 1 and M. A. Baldo, D. F. O'Brien, M. E. Thompson, S. R. Forrest, Phys. Rev. B 1999, 60, 14422). The prime reason for this is the high spin-orbit-coupling (SOC) of noble metal central ions (SOC constants Ir(III): ≈4000 cm$^{-1}$; Pt(II): ≈4500 cm$^{-1}$; Au(I): ≈5100 cm$^{-1}$; Ref.: S. L. Murov, J. Carmicheal, G. L. Hug, Handbook of Photochemistry, 2nd Edition, Marcel Dekker, New York 1993, p. 338 ff). Due to this quantum mechanical characteristic, the triplet-singlet transition, which is without SOC strictly forbidden for optical transitions, is allowed and an emission decay time of a few µs, small enough for OLED applications, is achieved.

Economically, it would be highly advantageous to replace the expensive noble metals with less expensive metals. Moreover, a large number of OLED emitter materials known to date are ecologically problematic, so that the use of less toxic materials is desirable. Copper(I) complexes are to be considered for this, for example. However, these have much smaller SOC values (SOC constants of Cu(I): ≈850 cm$^{-1}$, Ref.: S. L. Murov, J. Carmicheal, G. L. Hug, Handbook of Photochemistry, 2nd Edition, Marcel Dekker, New York 1993, p. 338 ff) than the central ions mentioned above. Therefore, the very important triplet-singlet-transitions of Cu(I)-complexes would be relatively strongly forbidden, and emission lifetimes, which are in the range of a few 100

μs to ms, would be too long for use in OLEDs. Such high emission decay times give rise to saturation effects with increasing current densities and the resulting occupation of a majority or of all emitter molecules. Consequently, further charge carrier streams can no longer lead completely to the occupation of the excited and emitting states. The result is then more unwanted ohmic losses. This leads to a distinct decline in efficiency of the OLED device with rising current density (called "roll-off" behavior). The effects of triplet-triplet annihilation and of self-quenching are similarly unfavorable (see, for example, H. Yersin, "Highly Efficient OLEDs with Phosphorescent Materials", Wiley-VCH, Weinheim 2008 and S. R. Forrest et al., Phys. Rev. B 2008, 77, 235215). For instance, disadvantages are found particularly in the case of use of such emitters for OLED illuminations where a high luminance, for example of more than 1000 cd/m², is required (cf.: J. Kido et al. Jap. J. Appl. Phys. 2007, 46, L10). Furthermore, molecules in electronically excited states are frequently more chemically reactive than in ground states so that the likelihood of unwanted chemical reactions increases with the length of the emission lifetime. The occurrence of such unwanted chemical reactions has a negative effect on the lifetime of the device.

Furthermore, Cu(I)-complexes generally undergo strong geometry changes after the excitation (through electron-hole recombination or through optical excitation) which leads to the reduction of emission quantum yields. Also, the emission colors are shifted due to these processes towards red, which is unwanted.

It was the object of the present invention to provide new materials that do not exhibit the disadvantages described above.

SUMMARY OF THE INVENTION

The object of the invention is met by copper(I) complexes (Cu(I) complexes), which are capable of emitting light and have a structure according to formula A

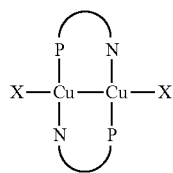

Formula A

In formula A, symbols represent as follows
Cu: Cu(I);
X: Cl, Br, I, SCN, CN, and/or alkynyl (R*—≡) (R* is defined like R);
P∩N: phosphine ligand substituted with a N-heterocycle, in particular having a structure according to formula B

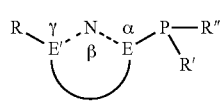

Formula B wherein:
E: a carbon or nitrogen atom;
E': a carbon or nitrogen atom which is not substituted with a hydrogen atom; dotted bond: a single bond or double bond;

R: alkyl group [$CH_3$—$(CH_2)_n$—], (n=0-20), optionally branched or substituted with halogens (F, Cl, Br, I), or
Aryl group (particularly phenyl), optionally substituted with alkyl groups, halogens (F, Cl, Br, I), silane (—$SiR*_3$) (R* defined like R1 below) or ether groups —OR (R defined like R1 below),
unsaturated group, such as, for example, alkenyl and alkynyl groups, optionally substituted with alkyl groups, halogens, (F, Cl, Br, I), silane (—$SiR*_3$) or ether groups —OR* (R*** defined like R1 below),
wherein R is no hydrogen atom;
R', R": alkyl groups [$CH_3$—$CH_2)_n$—] (n=0-20, preferably n>6), which can also be branched or cyclic, or
aryl or heteroaryl groups, which optionally are substituted with alkyl groups, halogens (F, Cl, Br, I), silane (—SiR*3) or ether groups —OR* (R* defined like R1), wherein R' and R" each are directly bound to the phosphorous atom of the phosphine ligand;
R1: defined like R, wherein R1 is optionally a hydrogen atom;
wherein R, R1 can optionally form annulated ring systems.

In a preferred embodiment of the invention R, R1, R' and/or R' (as well as the groups R2 and/or R3 defined further below) increase the solubility of the copper(I) complex in organic solvents. These substituents can also increase the hole and electron conduction of the complex. Appropriate hole and electron conductors are known to a person skilled in the art.

Furthermore, the invention relates to a copper(I) complex having a ΔE difference between the lowest triplet state and the singlet state above ($\Delta E(S_1-T_1)$ value) of 50 $cm^{-1}$ to 2000 $cm^{-1}$, preferably to smaller than 1500 $cm^{-1}$, more preferably to smaller than 1000 $cm^{-1}$, particularly preferably to smaller than 500 $cm^{-1}$. Such a copper(I) complex has a structure according to formula A without being restricted to this structure.

The copper(I) complex has preferably an emission quantum yield of greater than 20%, preferably greater than 40%, particularly preferably greater than 60%, most preferably greater than 80%. The copper(I) complex has preferably an emission life time of at the most 10 μs, preferably smaller than 6 μs, particularly preferably smaller than 3 μs. The copper(I) complex has preferably a solubility in organic solvents of at least 10 g/l.

In another aspect the invention relates to the use of a copper(I) complex as described herein for the emission of light, in particular in an emitter layer in an optoelectronic device.

Another aspect of the invention relates to a method for manufacturing an optoelectronic device wherein a copper(I) complex as described herein is used.

Preferably the method of manufacturing comprises wet-chemical steps, in particular depositing a first copper(I) complex dissolved in a first solvent onto a solid carrier, and depositing a second copper(I) complex dissolved in a second solvent onto the carrier, wherein the first copper(I) complex is not soluble in the second solvent, and the second copper(I) complex is not soluble in the first solvent. The first copper(I) complex and/or the second copper(I) complex are preferably a copper(I) complex according to formula A.

If the copper(I) complex has insufficient solubility, the processing of the complex can also be carried out using a dispersion.

Optionally, the method can further comprise the step of depositing a third copper(I) complex which is dissolved in the first solvent or in a third solvent onto a solid carrier, wherein the third copper(I) complex is a copper(I) complex according to formula A. In a preferred embodiment, the optoelectronic device is a white-light OLED, wherein the first copper(I) complex is a red-light emitter, the second copper(I) complex is a green-light emitter, and the third copper(I) complex is a blue-light emitter.

In a further aspect the invention relates to an electronic device comprising a binuclear (dual-core) copper(I) complex, having a ΔE difference between the lowest triplet state and the singlet state above it of between 50 cm$^{-1}$ and 2500 cm$^{-1}$, preferably between 50 cm$^{-1}$ and 2000 cm$^{-1}$, preferably between 50 cm$^{-1}$ and 1000 cm$^{-1}$, particularly preferably between 50 cm$^{-1}$ and 500 cm$^{-1}$. Such an optoelectronic device comprises in particular a copper(I) complex according to formula A.

In such an optoelectronic device, the amount of the copper(I) complex in an emitter layer of the device is 2 to 100% by weight, preferably 5 to 90% by weight or 5 to 100% by weight with regard to the total weight of the emitter layer. In case the optoelectronic device is an organic light emitting diode (OLED), the emitter layer preferably comprises a copper(I) complex formula A in the emitter layer, wherein the amount of the copper(I) complex in the emitter layer is between 2 to 100% by weight, preferably 5 to 90% by weight with regard to the total weight of the emitter layer.

The term "optoelectronic device" refers particularly to organic light emitting diodes (OLEDs), light-emitting electrochemical cells (LEECs or LECs), OLED-sensors, in particular gas and vapor sensors which are not hermetically sealed from the outside, optical temperature sensors, organic solar cells (OSCs), organic field-effect transistors, organic lasers, organic diodes, organic photo diodes and "down conversion" systems.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Exemplary embodiments of the invention will now be discussed in further detail. This invention may, however, be embodied in many different forms and should not be construed as limited to the embodiments set forth herein.

Surprisingly, the object of the invention is met by the copper(I) complexes (Cu(I) complexes) described herein. This means, the invention pertains to the provision of novel Cu(I) compounds, which show in particular the following characteristics:

relatively short emission lifetime of only a few μs,
high emission quantum yields of greater 40%, preferably of greater than 60%,
prevention of unwanted changes of geometry to a large extent, and
singlet harvesting.

Singlet Harvesting

It is of particular importance to loosen the strong transition prohibition from the excited triplet state T$_1$ to the singlet state S$_0$ in order to develop emitter molecules with shortest possible emission lifetime, yet high emission quantum yields. OLEDs using such emitters show a markedly diminished roll-off behavior of efficiency and furthermore provide for a longer operating life of the optoelectronic device.

Figure 1:
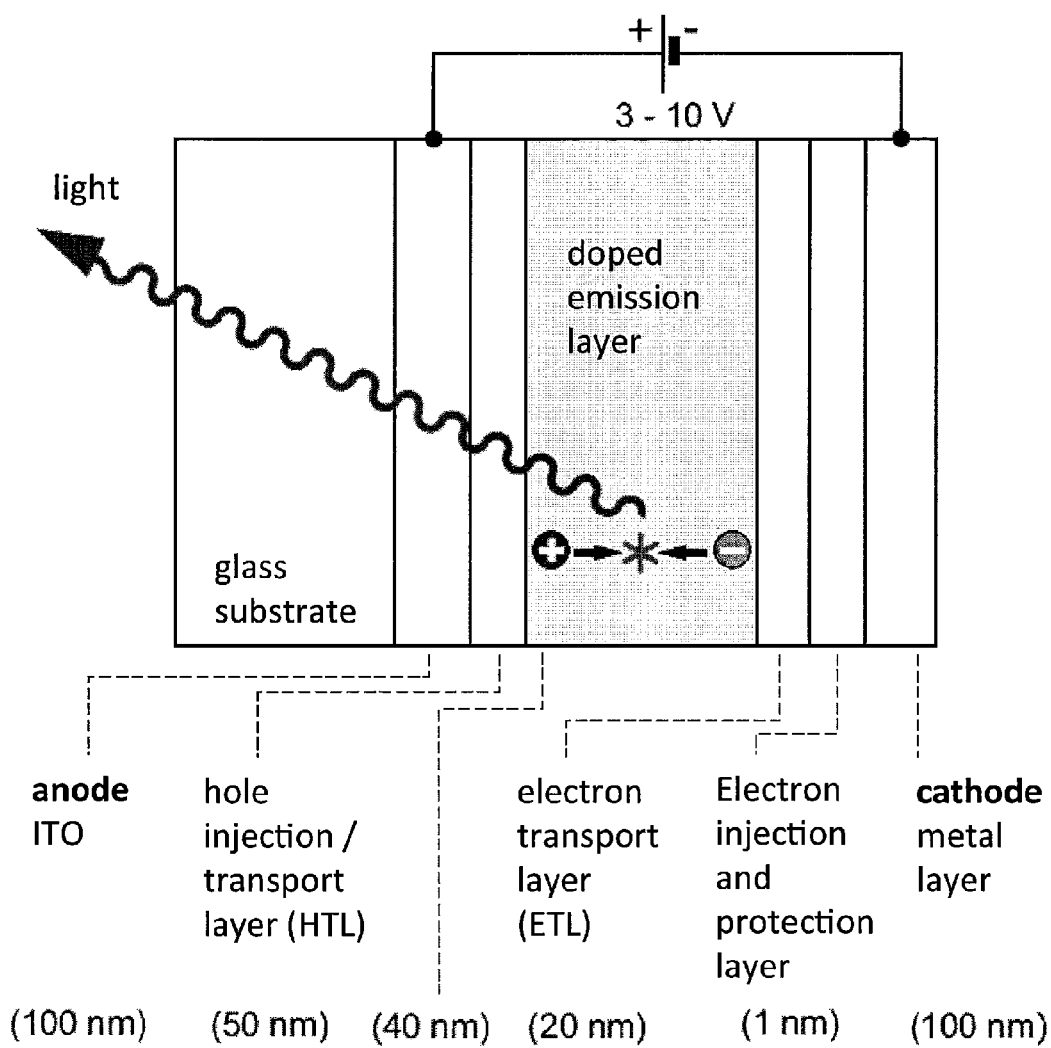
FIG. 1 shows a schematic structure of an OLED in accordance with an embodiment of the present invention. The figure is not drawn to scale.
Figure 2:
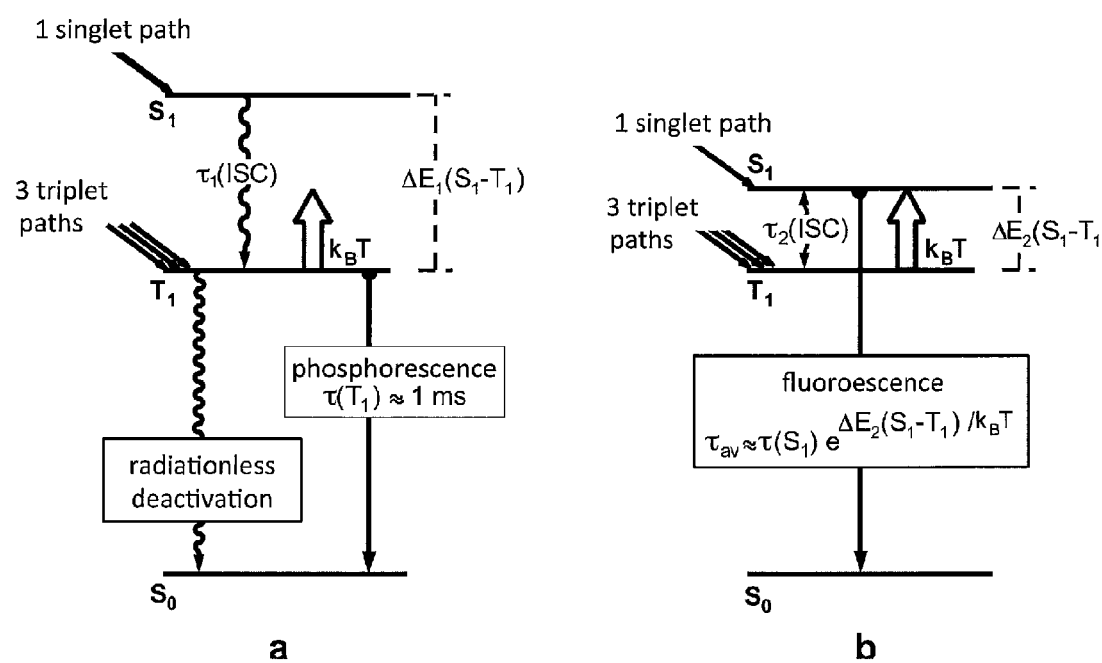
FIG. 2a shows an illustration of the electro luminescence behavior for binuclear Cu(I)-complexes in accordance with an embodiment of the present invention.
FIG. 2b shows an illustration of the electro luminescence behavior for transition metal complexes with a spin orbit coupling that is small or has a small effect in accordance with an embodiment of the present invention.

Surprisingly, the object described above is met by the present invention by using emitter molecules according to formula A that have particular electronic structures or comparatively small singlet-triplet-energy differences and that show according to the invention the singlet-harvesting effect described herein for binuclear Cu(I) complexes according to formula A. In FIG. 2a, a diagram of energy levels for transition metal complexes with spin orbit coupling that is either small or has only a small effect is depicted. The photo-physical electroluminescence properties of these molecules are described with reference to this diagram. Hole-electron recombination, as occurs, for example, in an opto-electronic component, leads, on statistical average, to 25% occupation of the singlet state (1 singlet path) and to 75% occupation of the triplet state (3 triplet paths) that lie at $\Delta E_1(S_1-T_1)$ below. The excitation into the $S_1$ state relaxes due to the intersystem crossing (ISC) process, which generally is faster than $10^{-12}$ s in transition metal organic complexes, into the $T_1$ state. The radiative emission lifetime of the triplet state is very long for these metal complexes of the first period of the transition metals (e.g., 100 µs to 1000 µs or longer). Emitters exhibiting such long emission decay times are hardly suitable for application in OLEDs.

According to the invention, the disadvantages of the state of the art described above can be avoided by choosing Cu(I) complexes that have an energy difference $\Delta E(S_1-T_1)$ between the lowest excited singlet state ($S_1$) and the triplet state ($T_1$) below it, of smaller than 2500 cm$^{-1}$. This is illustrated by the energy level diagram for Cu(I) complexes shown in FIG. 2b. This energy difference is small enough to enable thermal repopulation of the $S_1$ state from the $T_1$ state according to a Boltzmann distribution, or according to the thermal energy $k_BT$. Thus thermally activated light emission from the $S_1$-state can occur. This process proceeds according to equation (1)

$$\text{Int}(S_1 \to S_0)/\text{Int}(T_1 \to S_0) = k(S_1)/k(T_1)\exp(-\Delta E(S_1-T_1)/k_BT) \quad (1)$$

In this equation, $\text{Int}(S_1 \to S_0)/\text{Int}(T_1 \to S_0)$ is the intensity ratio of the emission from the $S_1$ state and the $T_1$ state. $k_B$ is the Boltzmann constant and T the absolute temperature. $k(S_1)/k(T_1)$ is the rate ratio of the corresponding conversion processes to the electronic ground state $S_0$. For Cu(I)-complexes, this ratio is between $10^2$ and $10^4$. Preferred in accordance with the invention are molecules having a rate ratio of about $10^3$ to $10^4$. $\Delta E(S_1-T_1)$ represents the energy difference $\Delta E_2(S_1-T_1)$ according to FIG. 2b.

The process of thermal repopulation described opens up an emission channel via the singlet state $S_1$ from the populated triplet. Since the transition from the $S_1$ to the $S_0$ state is strongly allowed, the triplet excitation energy is obtained virtually completely as light emission via the singlet state. The smaller the energy difference $\Delta E(S_1-T_1)$, the more marked this effect is. Preference is therefore given to Cu(I)-complexes having a $\Delta E=\Delta E(S_1-T_1)$ value between the lowermost excited singlet state and the triplet state below it of less than 1500 cm$^{-1}$, preferably less than 1000 cm$^{-1}$, more preferably of less than 500 cm$^{-1}$.

This effect is to be illustrated by a numerical example. Given a typical energy difference of $\Delta E(S_1-T_1)=800$ cm$^{-1}$, for room temperature applications (T=300 K) with $k_BT=210$ cm$^{-1}$ and a rate ratio of $10^3$, an intensity ratio according to equation (1) of approximately 20 is obtained. This means that the singlet emission process is dominant to an extreme degree for a molecule having these example values.

The emission lifetime of this example molecule also changes considerably. The thermal repopulation results in a mean lifetime $\tau_{av}$. This can be described by equation (2). Into a more detailed mathematical description is gone on the basis of eq. (4) stated further below.

$$\tau_{av} \approx \tau(S_1) \cdot \exp(\Delta E(S_1-T_1)/k_BT) \quad (2)$$

In this equation, $\tau(S_1)$ is the fluorescence lifetime without repopulation and $\tau_{av}$ is the emission lifetime, which is determined on opening of the repopulation channel by the two states $T_1$ and $S_1$ (see FIG. 2b). The other parameters have been defined above.

Equation (2) is again to be illustrated by a numerical example. For the assumed energy difference of $\Delta E(S_1-T_1)=800$ cm$^{-1}$ and a decay time of the fluorescing $S_1$ state of 50 ns, an emission decay time (of the two states) of $\tau_{av} \approx 2$ µs is obtained. This decay time is shorter than those of most very good Ir(III) or Pt(II) triplet emitters.

In summary, using this singlet harvesting process described herein for the first time for binuclear Cu(I) complexes it is thus possible in the ideal case to capture virtually all, i.e. a maximum of 100%, of the excitons and convert them to light via singlet emission. In addition, it is possible to shorten the emission decay time well below the value for pure triplet emitters of Cu(I) complexes, which is generally a few hundred µs to ms. Therefore, the use according to the invention of the respective complexes is particularly suitable for optoelectronic devices.

The binuclear Cu(I) complexes according to the invention having the above-described properties, i.e. having a small singlet-triplet energy difference $\Delta E(S_1-T_1)$, are preferably described with the general formula A given below. The electronic transitions that govern the optical properties of these complexes comprise a pronounced metal to ligand charge transfer character. This transition type correlates with a relatively small value of the quantum-mechanical exchange integral, which is known to a person of skill in the art. This results in the desired small energy difference $\Delta E(S_1-T_1)$.

The invention refers in another aspect to a method for selecting complexes, whose $\Delta E(S_1-T_1)$-value between the lowest exited singlet state ($S_1$) and the triplet state ($T_1$) below it is less than 2500 cm$^{-1}$, preferably less than 1500 cm$^{-1}$, particularly preferred less than 1000 cm$^{-1}$, most preferred less than 500 cm$^{-1}$.

The determination of the $\Delta E(S_1-T_1)$ value can either be performed by quantum-mechanical calculations using computer programs known in the art (for example, using Turbomole programs executing TDDFT calculations with reference to CC2 calculations) or determined experimentally, as explained below.

The energy difference $\Delta E(S_1-T_1)$, in particular of the complexes described by formula A can be described as an approximation by quantum-mechanical means via the so-called exchange integral multiplied by the factor 2. The value of the latter depends directly on the so-called charge-transfer-character under participation of the d-orbitals of the metal and the $\pi^*$-orbitals of the ligands. This means that an electronic transition between the different orbitals represents a metal-to-ligand charge transfer (CT) process. The smaller the overlap of the above-described molecular orbitals, the more marked is the electronic charge transfer character. This is then associated with a decrease in the exchange integral and hence a decrease in the energy difference $\Delta E(S_1-T_1)$. Due to these photo-physical (quantum-mechanical) properties, it is possible to achieve the energy differences according to the invention with $\Delta E(S_1-T_1)$ of less than 2500 cm$^{-1}$ or less than 1500 cm$^{-1}$ or less than 1000 cm$^{-1}$ or even less than 500 cm$^{-1}$.

The $\Delta E(S_1-T_1)$ value can be determined experimentally as follows:

For a given Cu(I) complex, the energy difference $\Delta E(S_1-T_1)$ can be determined in a simple manner using the above-specified equation (1). A rearrangement gives:

$$\ln\{\text{Int}(S_1 \to S_0)/\text{Int}(T_1 \to S_0)\} = \ln\{k(S_1)/k(T_1)\} - (\Delta E(S_1-T_1)/k_B)(1/T) \quad (3)$$

For the measurement of the intensities Int($S_1 \to S_0$) and Int($T_1 \to S_0$), it is possible to use any commercial spectrophotometer. A graphic plot of the (logarithmized) intensity ratios ln {Int($S_1 \to S_0$)/Int($T_1 \to S_0$)} measured at different temperatures against the reciprocal of the absolute temperature T generally gives a straight line. The measurement is conducted within a temperature range from room temperature (300 K) to 77 K or to 4.2 K, the temperature being established by means of a cryostat. The intensities are determined from the (corrected) spectra, Int($S_1 \to S_0$) and Int($T_1 \to S_0$) representing, respectively, the integrated fluorescence and phosphorescence band intensities, which can be determined by means of the programs provided with the spectrophotometer. The respective transitions (band intensities) can be identified easily since the triplet band is of lower energy than the singlet band and gains intensity with falling temperature. The measurements are conducted in oxygen-free diluted solutions (approx. $10^{-2}$ mol L$^{-1}$) or on thin films of the corresponding molecules or on films doped with the corresponding molecules. If the sample used is a solution, it is advisable to use a solvent or solvent mixture which forms glasses at low temperatures, such as 2-methyltetrahydrofuran, butyronitrile, toluene, ethanol or aliphatic hydrocarbons. If the sample used is a film, the use of a matrix having a much greater singlet and triplet energy than that of the Cu(I) complexes (emitter molecules), for example, PMMA (polymethyl methacrylate), is suitable. This film can be applied from solution.

The slope of the straight line is $-\Delta E(S_1-T_1)/k_B$. With $k_B = 1.380 \cdot 10^{-23}$ JK$^{-1}$ = 0.695 cm$^{-1}$ K$^{-1}$, it is possible to determine the energy separation directly.

A simple, approximate estimation of the $\Delta E(S_1-T_1)$ value can also be made by recording the fluorescence and phosphorescence spectra at low temperature (e.g. 77 K or 4.2 K using a cryostat). The $\Delta E(S_1-T_1)$ value then corresponds approximately to the energy difference between the high-energy slope flanks of the fluorescence and phosphorescence bands respectively.

Another method for determining the $\Delta E(S_1-T_1)$-value is through measuring the emission decay time with an instrument that is commercially available. Herein, the emission lifetime $\tau_{av}$ is measured using a cryostat for the range between 4.2 K or, e.g., 77 K and 300 K. Using formula (4) and the emission lifetime measured at low temperature for the triplet state $\tau(T_1)$, a fit of the measured values can be performed according to formula (4), yielding the $\Delta E(S_1-T_1)$-value. (The $\tau(T_1)$-value is often represented by the plateau arising when the measured values are plotted. In case such a plateau is seen, cooling to 4.2 K is generally no longer necessary. A corresponding example is given in FIG. 5)

$$\tau_{av} = \frac{3 + \exp\left(-\frac{\Delta E(S_1-T_1)}{k_B T}\right)}{\frac{3}{\tau(T_1)} + \frac{1}{\tau(S_1)}\exp\left(-\frac{\Delta E(S_1-T_1)}{k_B T}\right)} \quad (4)$$

The more pronounced the CT character of an organic molecule, the more the electronic transition energies change as a function of solvent polarity. Therefore, a strong polarity dependence of the emission energies provides an indication of small $\Delta E(S_1-T_1)$ values.

Stabilization of the Molecular Structure

Quadruple-coordinated Cu(I) complexes have an almost tetrahedral coordination of the metal atom in the electronic ground state. In case of excitation into an electronic excited state with pronounced metal-to-ligand charge-transfer character and the associated partial (further) oxidation of the metal atom, considerably changes in the geometry of the complex towards a "planarization" can occur. This process provides for a very effective mechanism for quenching luminescence and should therefore at least be suppressed to a large extent by stabilization of the molecular structure.

In the binuclear copper(I) complexes according to the invention, this quenching mechanism is strongly reduced or almost fully prevented by the very rigid molecular structure.

Chemical Lead Structure

The emitter of formula A according to the invention comprises the following characteristics:

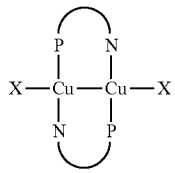

Formula A

P∩N is a phosphine ligand substituted with an N-heterocycle.

X=Cl, Br, I, SCN, CN, alkynyl (R*-≡) (R* defined like R below).

P∩N-phosphine ligands form with CuX (X=Cl, Br, I) binuclear complexes of ligand:Cu=3:2 stoichiometry. Surprisingly, substitution of the pyridine unit in 6-position with a methyl group results in a 1:1 stoichiometry, which is formed independently from the ratio and CuX. Thus the reaction of the P∩N ligand with Cu(I)X (X=Cl, Br, I), preferably in dichloromethane, preferably at room temperature, results in the binuclear 2:2 complex Cu$_2$X$_2$(P∩N)$_2$, in which the two Cu atoms are bridged via two P∩N ligands. This is due to the sterical overload of the ligand periphery, which prevents the coordination of another ligand effectively. There is no evidence that supports the formation of a 3:2 species, which changes over to a complex of formula A by rearrangement nor is the conversion of a known 3:2-complex without substitution in ortho position to the N atom into a 2:2-structure possible; only if a substituent is present in ortho position to the N atom binuclear complexes with short Cu—Cu distances are formed (with X=Cl: 3.078 Å; X=Br: 2.666 Å; X=I: 2.666 Å). This structure type represents a relatively rigid structure and thereby enables a distinct suppression of unwanted geometry changes in the electronically excited states.

The empirical formula of the complexes of formula A is similar to known copper(I) complexes Cu$_2$X$_2$(PR*R$_2$)$_2$ with X=Cl, Br, I and R=alkyl, alkenyl, aryl, etc. and R*=alkyl, alkenyl, aryl, heteroaryl, etc., whilst the spatial structure differs significantly thereof, since the P∩N-ligand acts as bidentate ligand and coordinates to Cu via P and N. Moreover, in the case of the Cu$_2$X$_2$(PR$_3$)$_2$ complexes there is a trifold coordinated Cu center, which is, due to the trigonal-planar structure, vulnerable to coordinating external molecules such as solvent molecules or free ligands, whereby the quantum yields can be strongly reduced. In addition, the complexation only via P in Cu$_2$X$_2$(PR$_3$)$_2$ results in a certain flexibility of the complex structure and possible dissociation of the monodentate P-ligand, whereby the stability of the complexes and the corresponding quantum yields are markedly reduced. This flexibility of the structure appears in the example of Cu$_2$I$_2$(PR$_3$)$_2$ with R=4-diphenylphosphine-1,5- diphenyl-1H-1,2,3-triazole, which results only by interaction of certain solvents such as ethyl acetate from a charged complex structure $Cu_3I_2PR_3$, which again is obtained from 3:2 stoichiometry of the reaction partners $PR_3$-ligand and CuI. Thus, in the end several structurally and in composition different complexes are obtained from a 3:2 reaction mixture, which can be converted into each other by interaction of certain solvents, indicating a low stability of the complexes.

In contrast, in complexes of formula A a tetrafold coordinated Cu-center is present due to the effect of the P∩N-ligand as bidentate ligand, whereby the metal center is well screened against external molecules and is strengthened by the substituent in γ-position. This leads to a very rigid and fixed molecule structure, in which quenching processes due to geometry changes are widely suppressed, which is reflected in a mostly high quantum yield. Furthermore, the rigid structure of the complexes of formula A with a distinct suppression of unwanted geometry changes in electronically excited states results in a smaller color shift of the emission in different complex surroundings (solid, in solution, in matrix) and smaller reduction of the emission quantum yields.

A structural similar complex, $Cu_2(P∩N)_2$, has due to the neutral P∩N-ligands the disadvantage that the complex is not neutral, but double positively charged, wherein non-coordinating negatively charged counter ions are necessary for charge equalization. This leads in part to problems during the manufacture and operation of common optoelectronic devices. The existence of the complexes as ionic compounds, for example, hinders their dissolving in solvents suitable for OLED manufacture such as toluene, mesitylene, chlorobenzene etc. and while operating a common OLED, the charged emitter and/or their corresponding counter ions could lead to unwanted ion migration due to the high electric strengths. In contrast, the complex of formula A is an electrical neutral Cu complex, since the charge equalization is assured by the X-molecules directly coordinated to the Cu atoms and the neutral complex therefore does not migrate in the electric field of an OLED.

Phosphine Ligand P∩N

The P∩N-ligand is a phosphine ligand functionalized with an N-heterocycle, wherein—as seen from the phosphorous atom—a nitrogen atom is in β-position and the atom E' is not substituted with a hydrogen atom in γ-position. E and E' are either a carbon or a nitrogen atom. The bond to the copper atoms is formed via the nitrogen atom in position β and via the phosphorous atom. The dotted bonds are either a single bond or a double bound depending on the N-heterocycle. Formula B shall illustrate this:

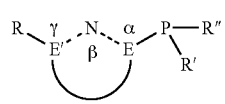

Formula B

Definition of the N-Heterocycle:

The N-heterocycle is preferably a pyridine group, which is substituted in 6-position with R, and further N-heterocyclic 6-membered rings and their annulated homologs:

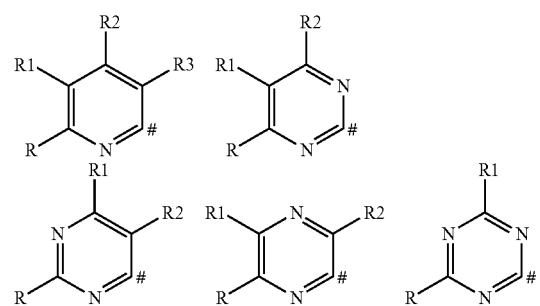

The N-heterocycle is linked to the phosphorous atom at the position labeled with "#". The substituent R can be an alkyl group $[CH_3—(CH_2)_n—]$ (n=0-20), which can also be branched or substituted with halogens (F, Cl, Br, I) or an aryl group (particularly phenyl), which can be substituted with alkyl groups, halogens (F, Cl, Br, I), silane ($—SiR*_3$) or ether groups $—OR$ ($R$ defined like R1). Likewise, R can be an unsaturated group such as alkenyl and alkynyl, which can again be substituted with alkyl groups, halogens (F, Cl, Br, I), silane ($—SiR*_3$) or ether groups $—OR*$ ($R***$ defined like R1). R shall not be a hydrogen atom.

The substituents R1-R3 are defined like R, except that these substituents can also be hydrogen atoms. The substituents R, R1-R3 can also lead to annulated ring systems.

Some examples for possible N-heterocycles are to be illustrated by the general formulae:

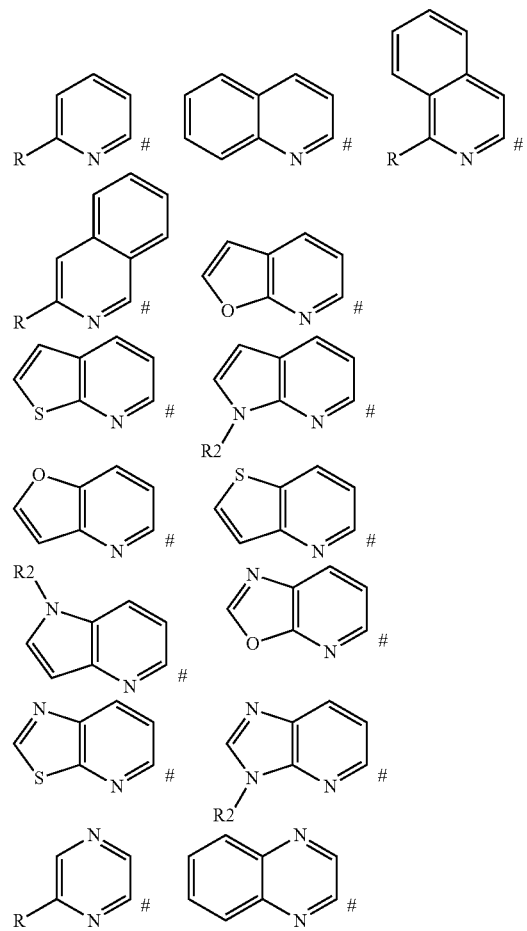

-continued

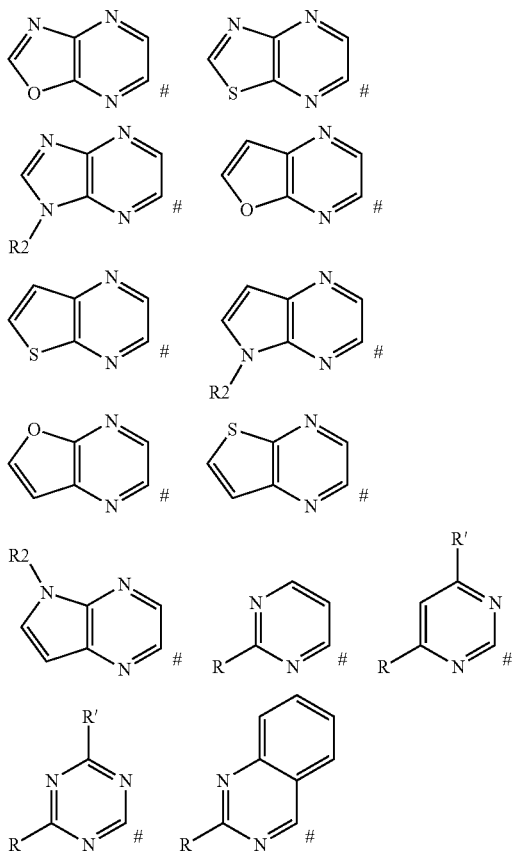

The N-heterocycles can also be 5-membered rings:

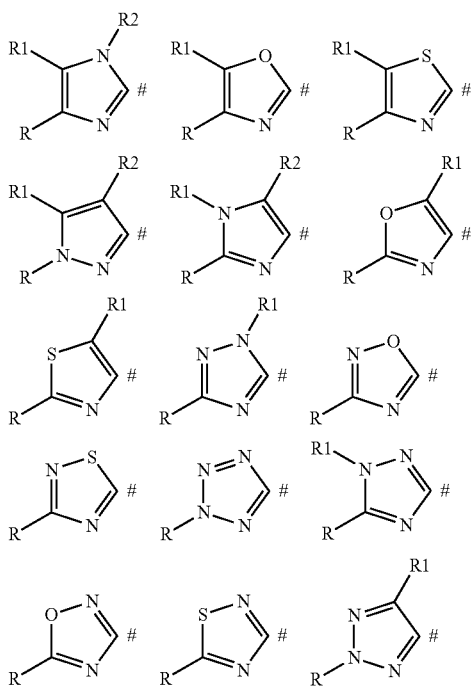

The groups R, R1 and R2 are defined as above.

The following ligands are preferred:

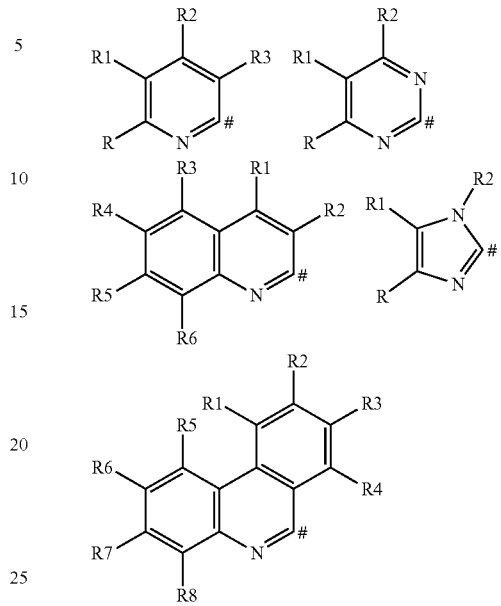

The groups R, R1 to R8 are defined as above.

Definition of the Group R' and R":

The groups R' and R", which are directly bound to the phosphorous atom of the phosphine ligand, are alkyl groups [$CH_3$—($CH_2$)$_n$—] (n=0-20, preferably n>6), which can also be branched or cyclic, or aryl and heteroaryl groups, which can be substituted with alkyl groups, halogens (F, Cl, Br, I), silane (—$SiR*_3$) or ether groups —OR* (R* defined like R1). Particularly preferred are phenyl groups.

Solubility

When manufacturing optoelectronic devices using wet-chemical processes, it is advantageous to specifically regulate the solubility. Thereby, the complete or partial dissolution of a layer already deposited can be avoided. By introducing special substituents, the solubility characteristics can be strongly influenced. It is possible to use orthogonal solvents that dissolve only the substance of the instant manufacturing step, but not the substances of the layer(s) below. For this purpose, the substituents R, R1-R3, R' and R" can be chosen such that they allow tuning of the solubilities. The following possibilities for selecting corresponding substituents are given:

Solubility in Nonpolar Media

Nonpolar substituents R, R1-R3, R' and R" increase the solubility in nonpolar solvents and decrease the solubility in polar solvents. Nonpolar groups are, e.g. alkyl groups [$CH_3$—($CH_2$)$_n$—] (n=1-30), also branched, substituted alkyl groups, e.g. with halogens. In particular: partially or perfluorinated alkyl groups as well as perfluorinated oligo- and polyethers, e.g. [—($CF_2$)$_2$—O]$_n$— and (—$CF_2$—O)$_n$— (n=2-500). Further nonpolar groups are: ethers —OR*, thioethers —SR*, differently substituted silanes $R*_3Si$— (R*=alkyl or aryl), siloxanes $R*_3Si$—O—, oligosiloxanes R(—$R_2Si$—O)$_n$—(R=R*, n=2-20), polysiloxanes R** (—$R*_2Si$—O)$_n$— (n>20); oligo/polyphosphazenes R**(—$R*_2P$=N—)$_n$— (n=1-200).

Solubility in Polar Media

Polar substituents R, R1-R3, R' and R" increase the solubility in polar solvents. These can be:

Alcohol groups: —OH

Carboxylic acids, phosphonic acids, sulfonic acid groups as well as their salts and esters (R*=H, alkyl, aryl, halogen; cations: alkali metals, ammonium salts): —COOH, —P(O)(OH)$_2$, —P(S)(OH)$_2$, —S(O)(OH)$_2$, —COOR*, —P(O)(OR*)$_2$, —P(S)(OR*)$_2$, —S(O)(OR*)$_2$, —CONHR*, —P(O)(NR*$_2$)$_2$, —P(S)(NR*$_2$)$_2$, —S(O)(NR*$_2$)$_2$ Sulfoxides: —S(O)R*, —S(O)$_2$R*

Carbonyl groups: —C(O)R*

Amines: —NH$_2$, NR*$_2$, —N(CH$_2$CH$_2$OH)$_2$,

Hydroxylamines=NOR*

Oligoesters, —O(CH$_2$O—)$_n$, —O(CH$_2$CH$_2$O—)$_n$ (n=2-200)

Positively charged substituents: e.g. ammonium salts —N$^+$R*$_3$X$^-$, phosphonium salts —P$^+$R*$_3$X$^-$ Negatively charged substituents: e.g. borates —(BR*$_3$)$^-$, aluminates —(AlR*$_3$)$^-$ (the anion can be an alkali metal or ammonium ion).

In order to avoid the presence of freely movable ions, positively and negatively charged substituents can also be united in the substituents R, R1-R3, R' and R".

EXAMPLES

General Synthesis Procedure

Synthesis of the Binuclear Cu(I) Complexes According to Formula a.

The corresponding copper halide is provided in dichloromethane and one equivalent of the phosphine ligand is added. The reaction mixture is stirred over night at room temperature. After filtration the complex is obtained as fine-crystalline yellow precipitate by addition of Et$_2$O. Crystals suitably for X-ray structure analysis are obtained by slow gas phase diffusion of Et$_2$O into the reaction solution.

I. P∩N*=6-MePyrPPh$_2$, 1: Cu$_2$X$_2$(6-MePyrPPh$_2$)$_2$, 2a-c

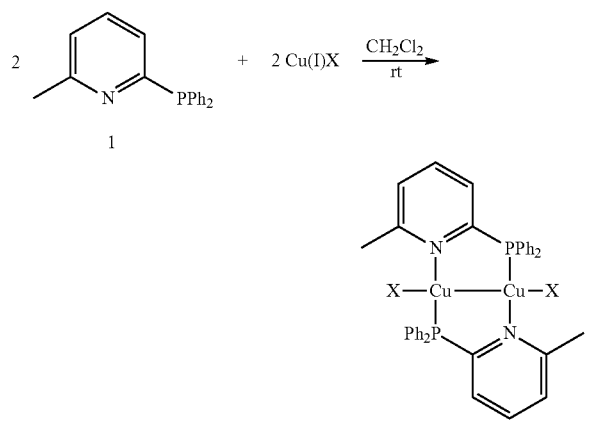

2a: X = Cl
2b: X = Br
2c: X = I

TABLE 1

Elemental analyses

|  | C | | H | | N | |
|---|---|---|---|---|---|---|
|  | calc. | found | calc. | found | calc. | found |
| 2a | 57.45 | 57.44 | 4.29 | 4.30 | 3.72 | 3.63 |
| 2b | 57.97 | 57.97 | 4.32 | 4.52 | 3.76 | 3.64 |
| 2c | 46.22 | 45.93 | 3.45 | 3.44 | 2.99 | 3.48 |

(calc. = calculated)

Photophysical Characterization

Figure 3:
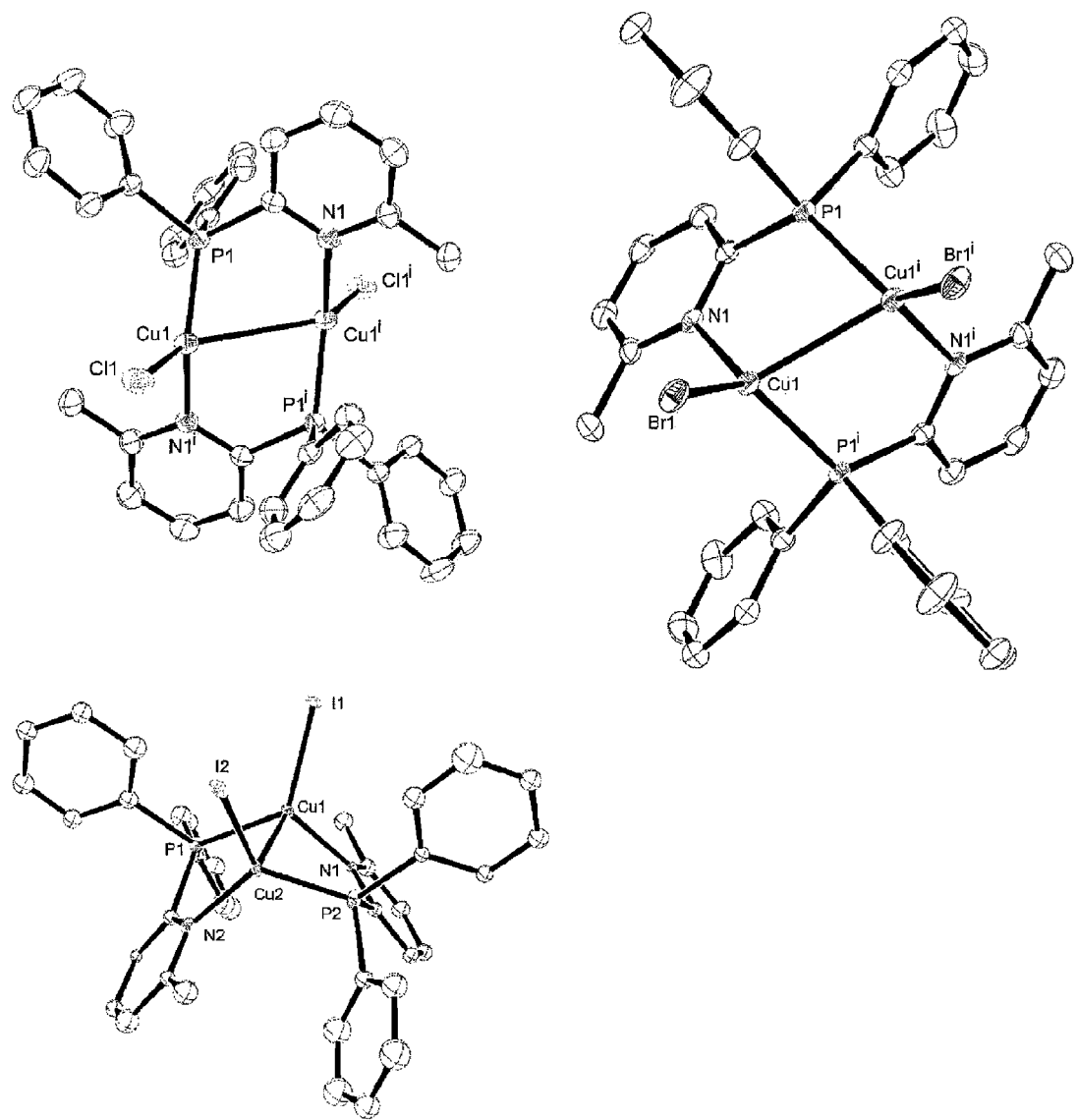
FIG. 3 shows molecular structures of the dimeric copper complexes (6-Me-py)PPh$_2$)$_2$Cu$_2$X$_2$ (X=Cl, Br, D in accordance with an embodiment of the present invention.

In FIG. 3 the molecular structures of the three synthesized binuclear Cu(I) complexes, which result from crystal structure analyses, are shown.

Figure 4:
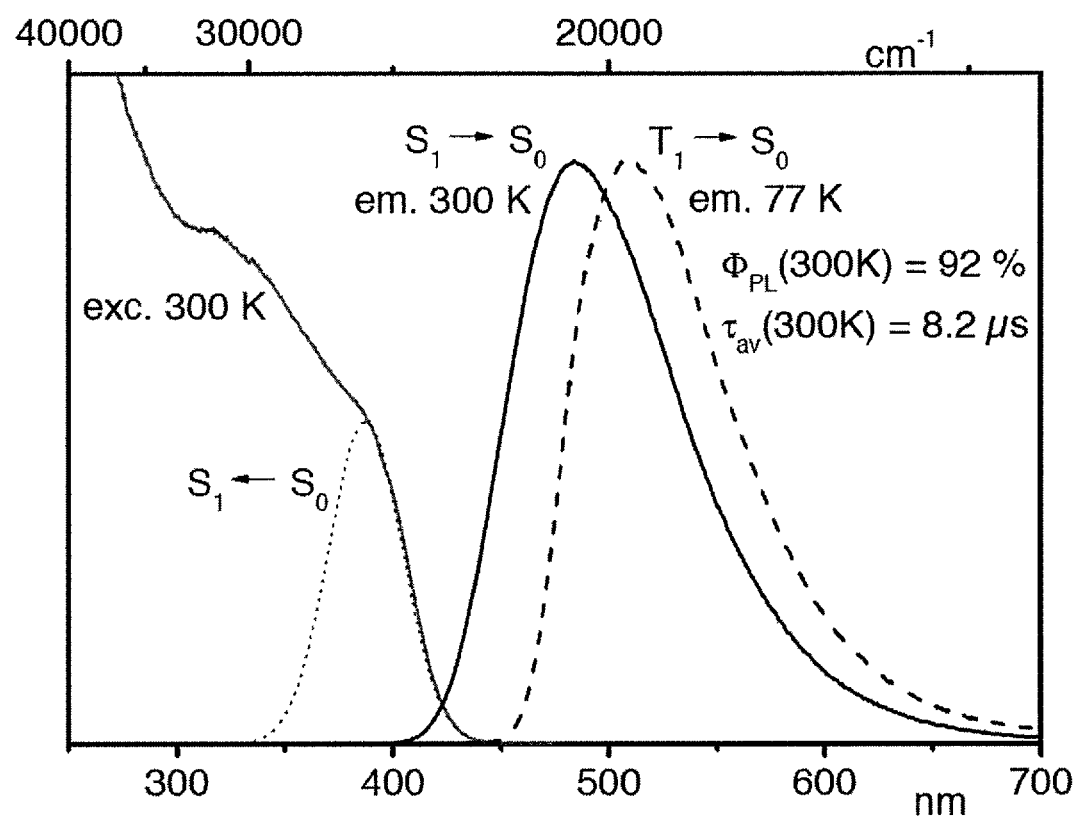
FIG. 4 shows the excitation and emission spectrum of Cu$_2$Cl$_2$((6-Me-py)PPh$_2$)$_2$ in accordance with an embodiment of the present invention.
Figure 5:
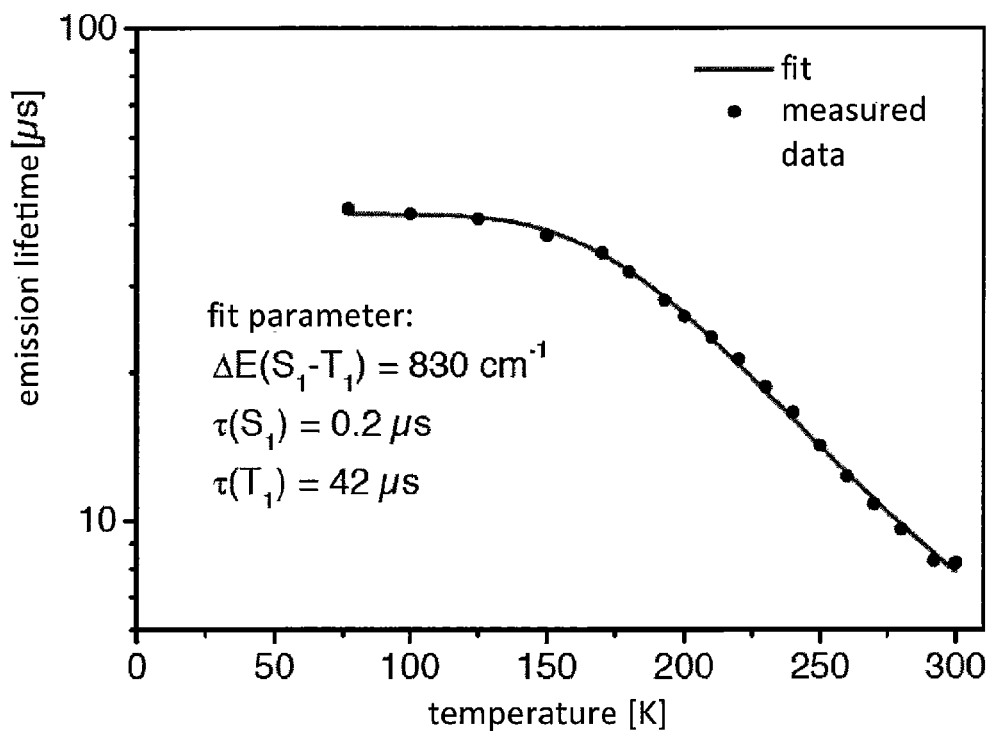
FIG. 5 shows the temperature profile of the emission life decay time of Cu$_2$Cl$_2$((6-Me-py)PPh$_2$)$_2$ in accordance with an embodiment of the present invention.

In FIG. 4, the emission spectra for T=300 K and 77 K and the excitation spectra for T=300 K for Cu$_2$Cl$_2$(Ph$_2$PMepy)$_2$ (2a) are shown. FIG. 5 shows the temperature response of the measured decay time in the range of T=77 K to 300 K. On the basis of these results, the occurrence of the singlet harvesting effect can be concluded. At T=77 K only the energetically lower lying triplet state T$_1$ emits with a (in this case comparably short) decay time of 42 µs (FIG. 5, table 3). With increasing temperature the energetically higher lying singlet (S$_1$) state is increasingly thermally re-occupied. At room temperature the decay time is 8.2 µs (table 2). The measured decay characteristics can be described by eq. (4). An energy difference between the triplet state T$_1$ and the singlet state S$_1$ of 830 cm$^{-1}$ results from a corresponding fit procedure. The intrinsic decay time of the S$_1$ state results in τ(S$_1$)=0.2 µs. These results are summarized in FIG. 6. Due to this process of reoccupation from the T$_1$ state, which represents a long-living reservoir, into the short-living S$_1$ state a (measured) two-states-system decay time of τ(300 K)=8.2 µs results (table 2). Moreover, a blue-shift of the emission (shift to higher energy) occurs with the thermally induced occupation of the energetically higher lying S$_1$ state (FIG. 4). This result also indicates the presence of the singlet harvesting in the binuclear Cu(I) complex according to the invention Cu$_2$Cl$_2$(Ph$_2$PMepy)$_2$. It should be particularly pointed out that the emission quantum yield $\phi_{PL}$(300 K)=92% measured for this compound is extremely high.

Figure 19:
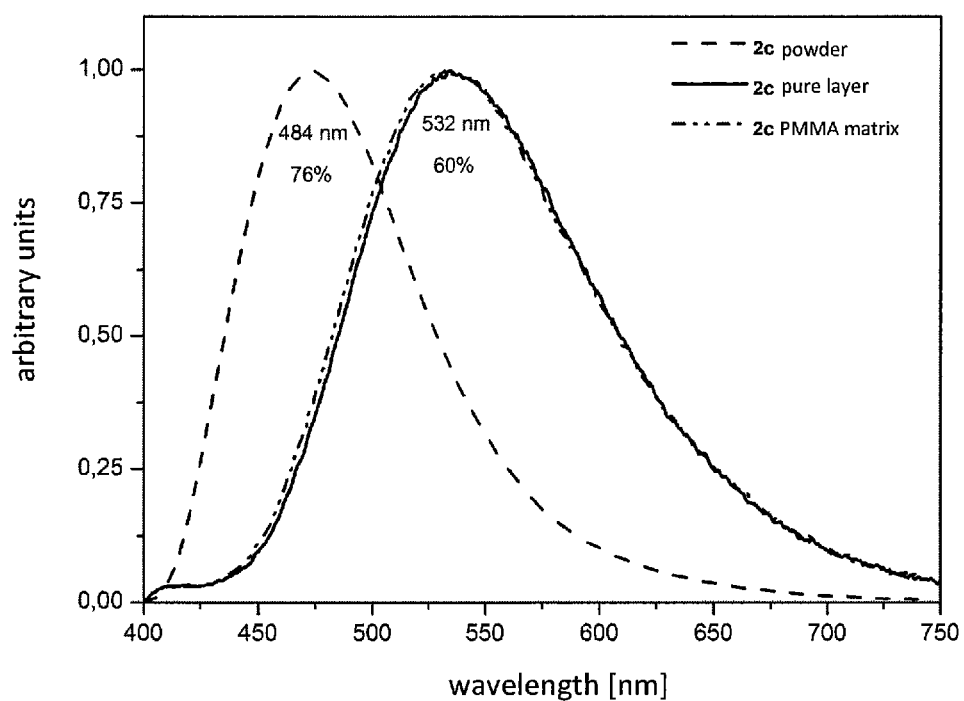
FIG. 19 shows the emission spectrum and emission quantum yield of complex 2c as a powder sample in accordance with an embodiment of the present invention.

Furthermore, the rigid structure of the complexes of formula A with a marked suppression of unwanted geometry changes in the electronically excited states leads to in a smaller color shift of the emission in different complex surroundings (solid, as film, in matrix) and smaller reduction of the emission quantum yields (FIG. 19, shown in example 2c).

Figure 7:
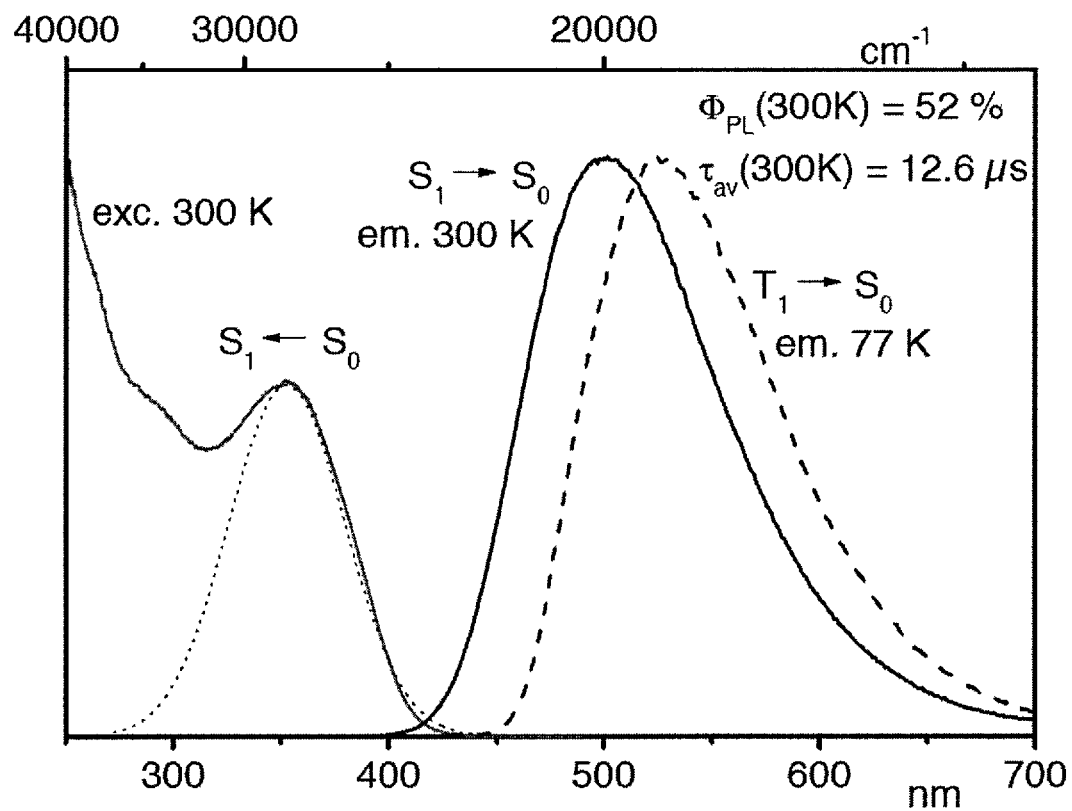
FIG. 7 shows the excitation and emission spectrum of Cu$_2$Br$_2$((6-Me-py)PPh$_2$)$_2$ in accordance with an embodiment of the present invention.
Figure 8:
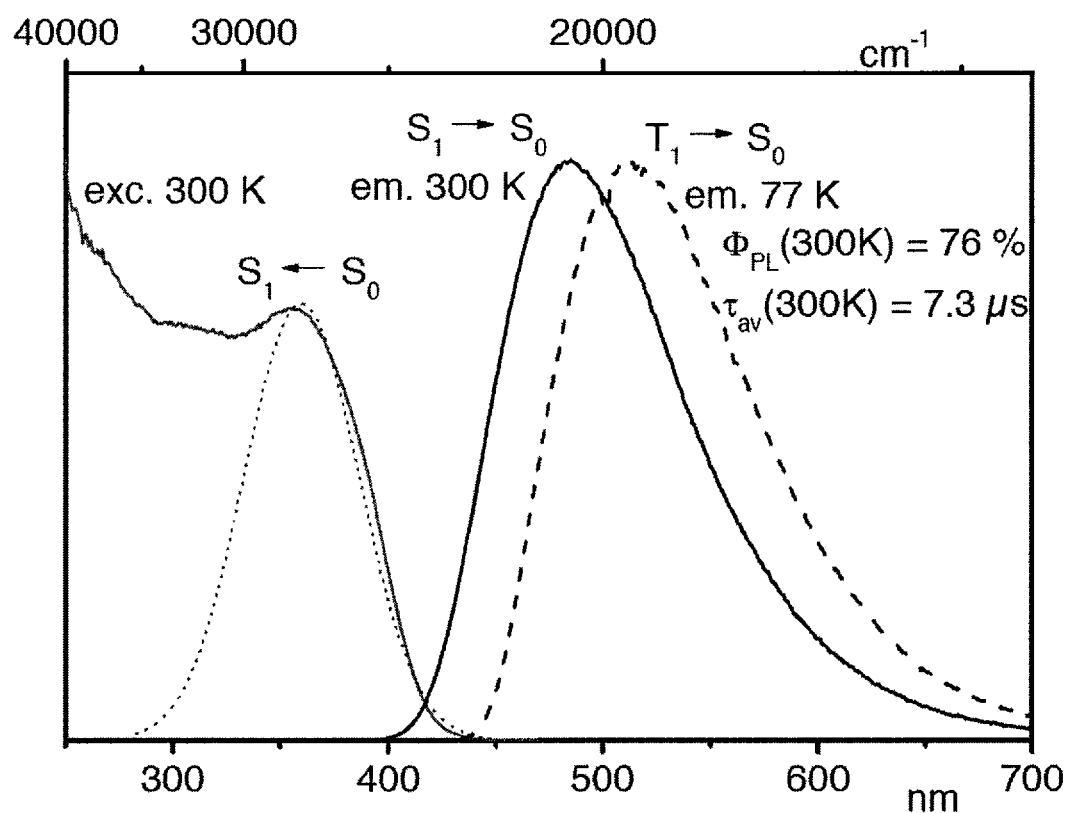
FIG. 8 shows the excitation and emission spectrum of Cu$_2$I$_2$((6-Me-py)PPh$_2$)$_2$ in accordance with an embodiment of the present invention.

In FIGS. 7 and 8 as well as tables 2 and 3, the corresponding spectra and data for the complexes Cu$_2$Br$_2$(Ph$_2$PMepy)$_2$ (2b) and Cu$_2$I$_2$(Ph$_2$PMepy)$_2$ (2c) are summarized. These experimentally obtained results suggest also the appearance of a distinct singlet harvesting effect in these two binuclear complexes.

TABLE 2

Photophysical data at 300 K (powder data)

|  | $\lambda_{max}$(300 K) [nm] | $\phi_{PL}$ (300 K) [b] | τ(300 K)[a] [µs] | k$^r$(300 K) [s$^{-1}$] | k$^{nr}$(300 K) [s$^{-1}$] |
|---|---|---|---|---|---|
| 2a | 485 | 0.92 | 8.2 | 1.1 × 10$^5$ | 1.0 × 10$^4$ |
| 2b | 501 | 0.52 | 12.6 | 4.1 × 10$^4$ | 3.8 × 10$^4$ |
| 2c | 484 | 0.76 | 7.3[c] | 1.0 × 10$^5$ | 3.3 × 10$^4$ |

TABLE 3

Photophysical data at 77 K (powder data)

| | $\lambda_{max}$ (77 K) [nm] | $\Phi_{PL}$ (77 K)[b] | $\tau$ (77 K)[a] [μs] | $k^r$ (77 K) [s$^{-1}$] | $k^{nr}$ (77 K) [s$^{-1}$] |
|---|---|---|---|---|---|
| 2a | 510 | 0.97 | 42 | $2.2 \times 10^4$ | $6.6 \times 10^3$ |
| 2b | 526 | | 88 | | |
| 2c | 511 | 0.84 | 51[c] (≈160[d]) | $1.6 \times 10^4$ ($5.3 \times 10^3$) | $3.6 \times 10^3$ ($1.0 \times 10^3$) |

[a] Excitation wavelength $\lambda_{exc} = 372$ nm
[b] Excitation wavelength $\lambda_{exc} = 400$ nm
[c] The decay curve deviates from monoexponential behavior. The decay time was determined by a biexponentional best-fit curve.
[d] Long component II. P∩N*=4,6-DiMePyrimPPh$_2$, 3: Cu$_2$X$_2$(4,6-DiMePyrimPPh$_2$)$_2$, 4a,b

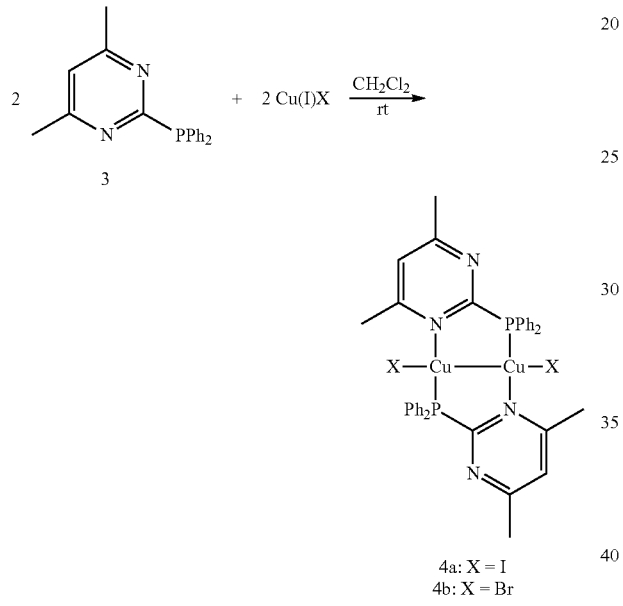

4a: X = I
4b: X = Br

TABLE 3

Elemental analyses

| | C | | H | | N | |
|---|---|---|---|---|---|---|
| | calc. | found | calc. | found | calc. | found |
| 4a | 44.78 | 44.94 | 3.55 | 3.50 | 5.80 | 5.75 |
| 4b | 49.61 | 49.49 | 3.93 | 3.90 | 6.43 | 6.26 |

(calc. = calculated)

Photophysical Characterization

Figure 9:
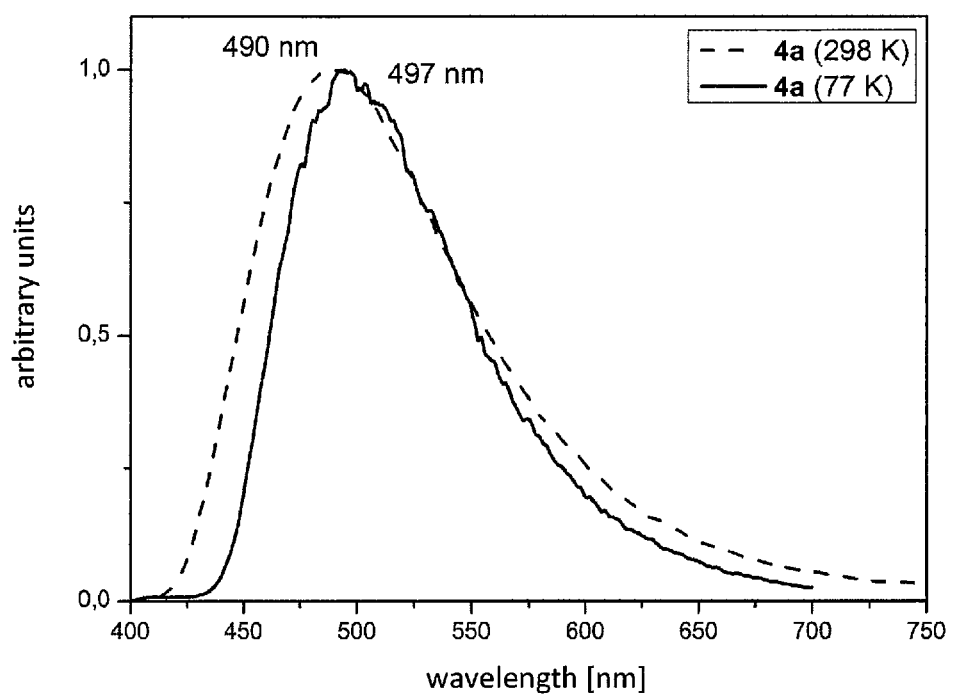
FIG. 9 shows the emission spectra of powder samples of complex 4a in accordance with an embodiment of the present invention.

The emission spectrum of 4a at 298 K is shown in FIG. 9.

The emission spectrum of 4a at 77 K is shown in FIG. 9.

The emission quantum yield of 4a at 298 K is 26% (measured with Hamamatsu C9920-02G)

The emission lifetime of 4a is 3 μs (Horiba Fluoromax 4 with TCSPC).

The ΔE(S1–T$_1$)-value of 4a is 290 cm$^{-1}$ (determined by the energy difference of the fluorescence and phosphorescence band at 298 K and 77 K, respectively).

Figure 10:
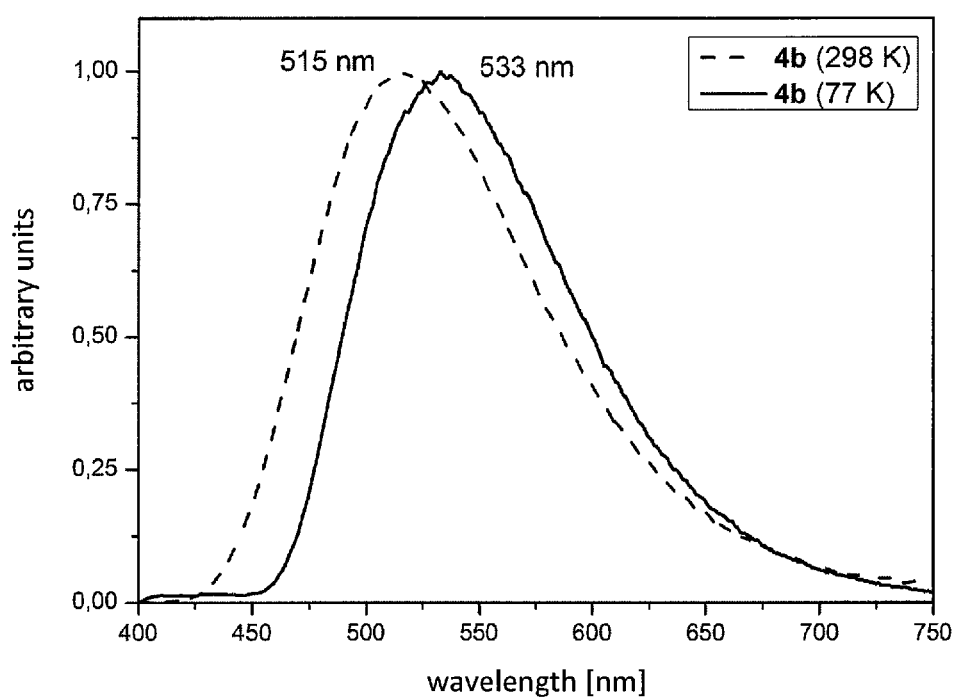
FIG. 10 shows the emission spectra of powder samples of complex 4b in accordance with an embodiment of the present invention.

The emission spectrum of 4b at 298 K is shown in FIG. 10.

The emission spectrum of 4b at 77 K is shown in FIG. 10.

The emission quantum yield of 4b at 298 K is 21% (measured with Hamamatsu C9920-02G)

The emission lifetime of 4b is 5 μs (Horiba Fluoromax 4 with TCSPC).

The ΔE(S1–T1)-value of 4b is 660 cm$^{-1}$ (determined by the energy difference of the fluorescence and phosphorescence band at 298 K and 77 K, respectively).

III. P∩N*=4-iBu-6-MePyrimPPh$_2$, 5: Cu$_2$X$_2$(4,6-DiMePyrimPPh$_2$)$_2$, 6a,b

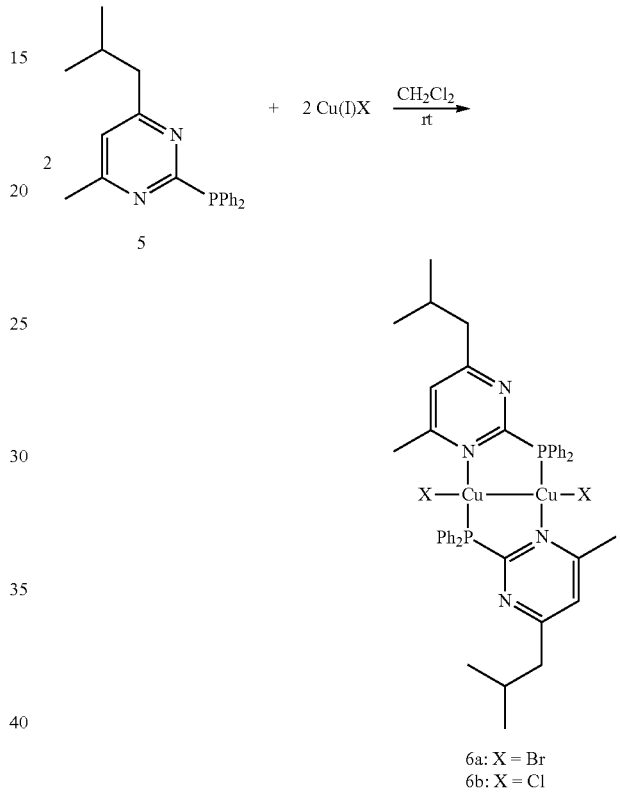

6a: X = Br
6b: X = Cl

Photophysical Characterization

Figure 11:
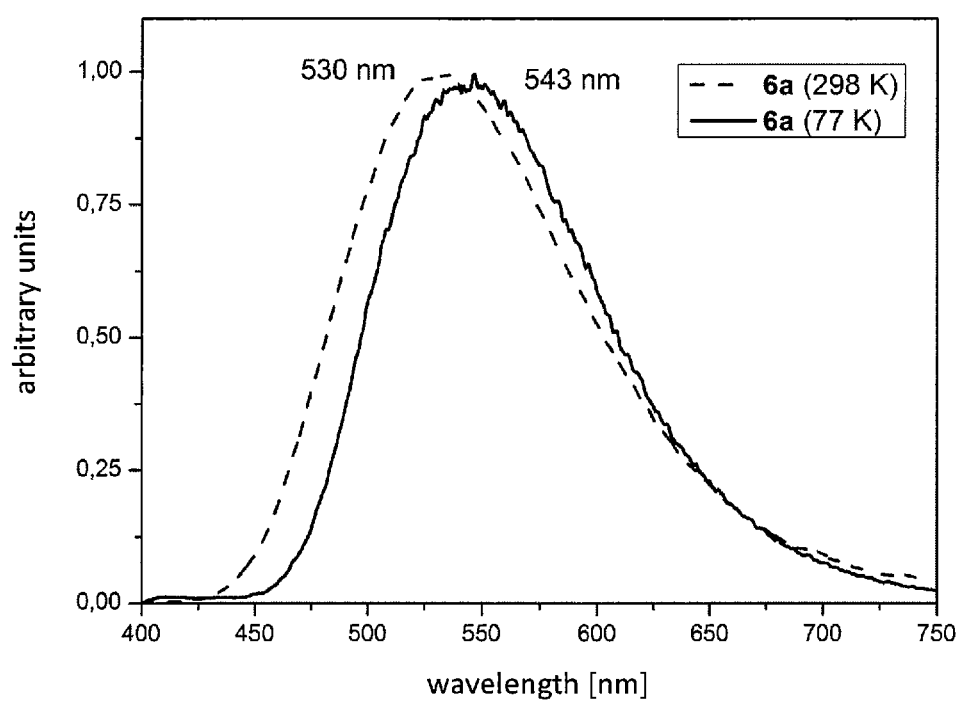
FIG. 11 shows the emission spectra of powder samples of complex 6a in accordance with an embodiment of the present invention.

The emission spectrum of 6a at 298 K is shown in FIG. 11.

The emission spectrum of 6a at 77 K is shown in FIG. 11.

The emission quantum yield of 6a at 298 K is 24% (measured with Hamamatsu C9920-02G)

The emission lifetime of 6a is 15 μs (Horiba Fluoromax 4 with TCSPC).

The ΔE(S1–T1)-value of 6a is 450 cm$^{-1}$ (determined by the energy difference of the fluorescence and phosphorescence band at 298 K and 77 K, respectively).

Figure 12:
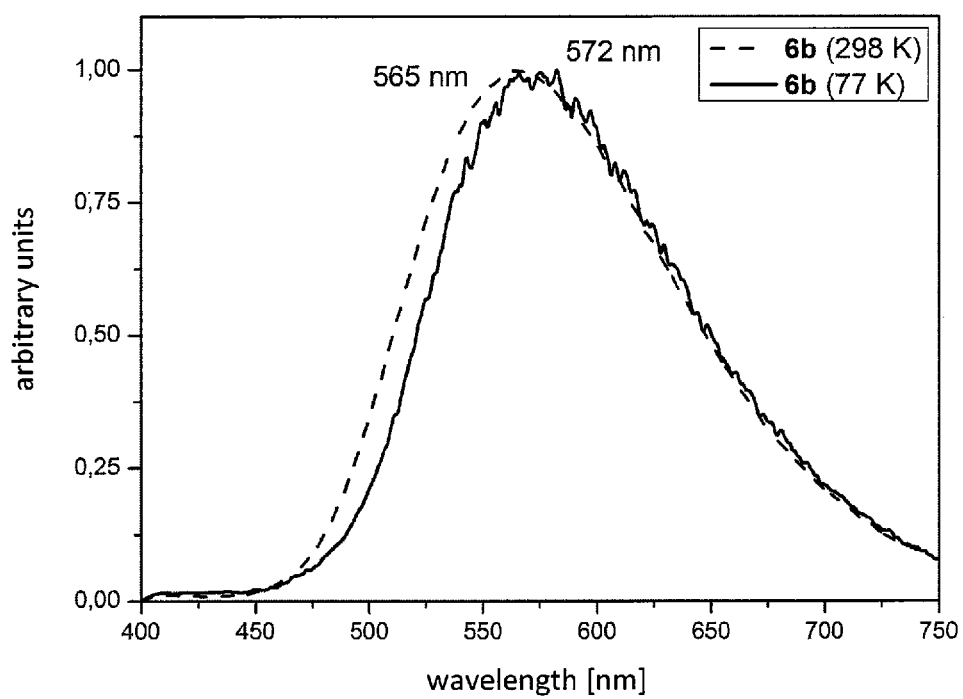
FIG. 12 shows the emission spectra of powder samples of complex 6b in accordance with an embodiment of the present invention.

The emission spectrum of 6b at 298 K is shown in FIG. 12.

The emission spectrum of 6b at 77 K is shown in FIG. 12.

The emission quantum yield of 6b at 298 K is 22% (measured with Hamamatsu C9920-02G)

The emission lifetime of 6b is 11 μs (Horiba Fluoromax 4 with TCSPC).

The ΔE(S1–T1)-value of 6b is 220 cm$^{-1}$ (determined by the energy difference of the fluorescence and phosphorescence band at 298 K and 77 K, respectively).

IV. P∩N*=4-Me-1-PentImidazolePPh$_2$, 7: Cu$_2$I$_2$(4-Me-1-PentImidazolePPh$_2$)$_2$, 8a

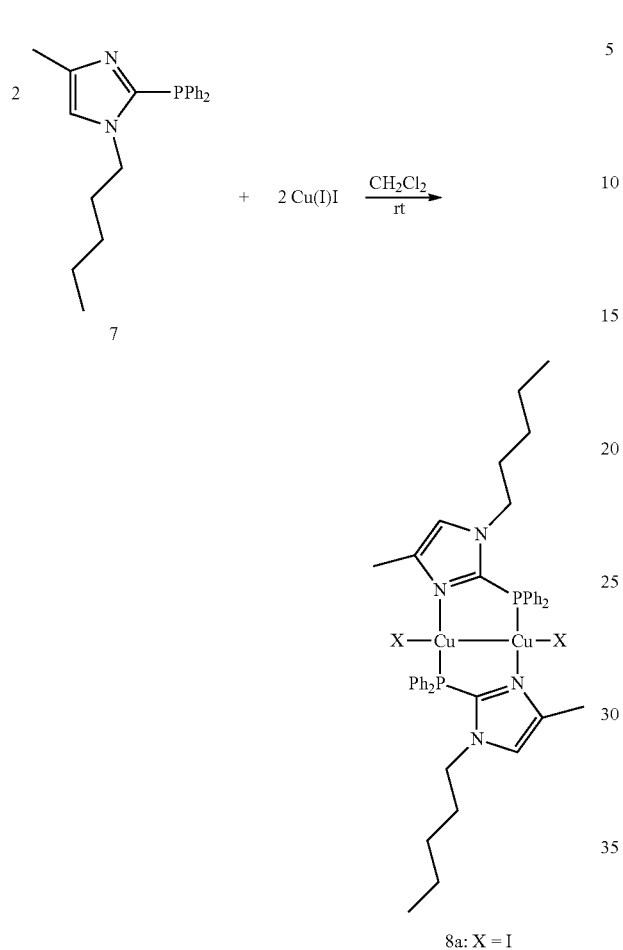

8a: X = I

V. P∩N*=4-Me-1-TolylImidazolePPh$_2$, 9: Cu$_2$I$_2$(4-Me-1-TolylImidazolePPh$_2$)$_2$, 10a

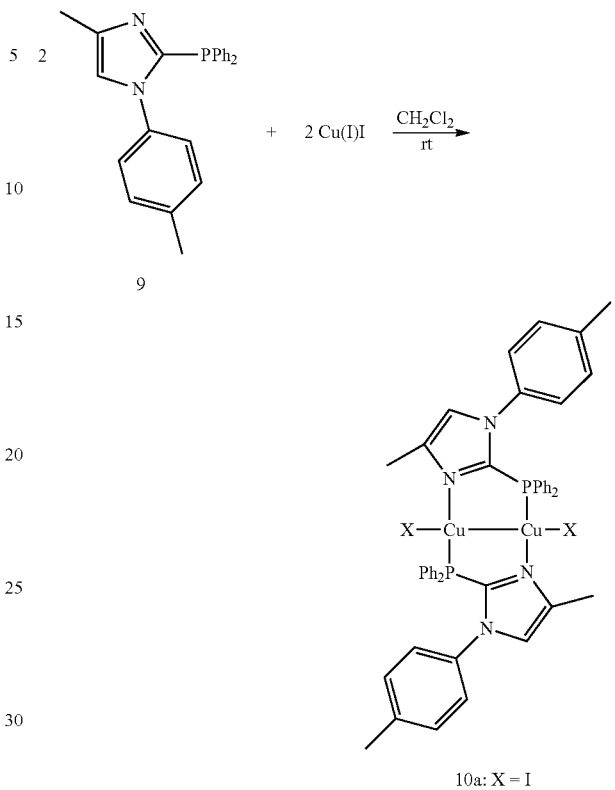

10a: X = I

TABLE 4

Elemental analysis

|  | C | | H | | N | |
|---|---|---|---|---|---|---|
|  | calc. | found | calc. | found | calc. | found |
| 8a | 47.87 | 47.83 | 4.78 | 4.68 | 5.32 | 5.29 |

(calc. = calculated)

Photophysical Characterization

Figure 13:
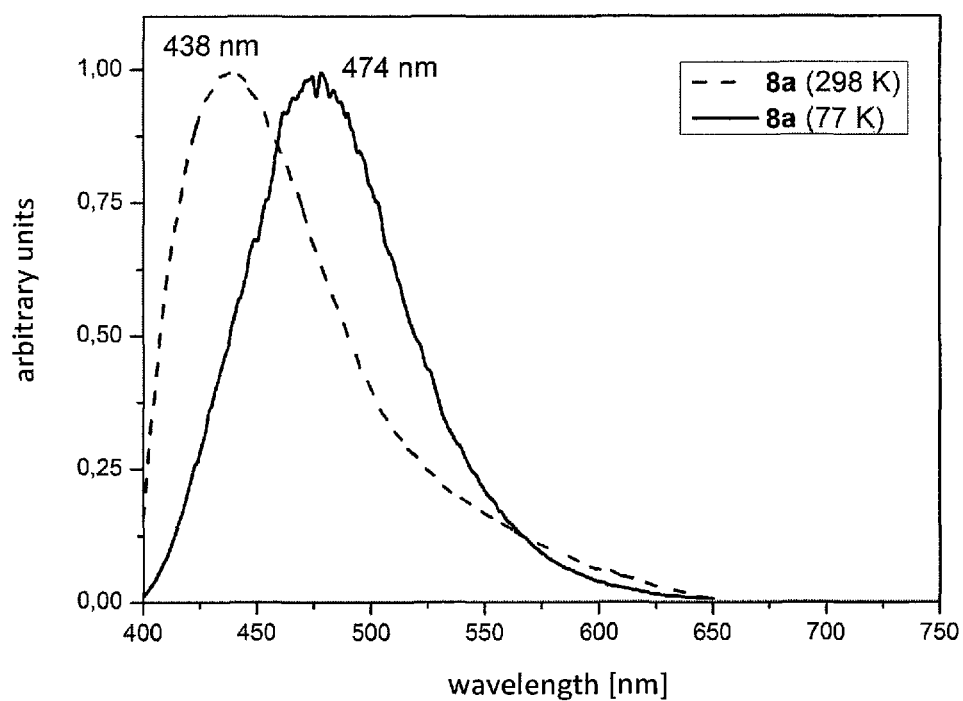
FIG. 13 shows the emission spectra of powder samples of complex 8a in accordance with an embodiment of the present invention.

The emission spectrum of 8a at 298 K is shown in FIG. 13.

The emission spectrum of 8a at 77 K is shown in FIG. 13.

The emission quantum yield of 8a at 298 K is 27% (measured with Hamamatsu C9920-02G)

The emission lifetime of 8a is 4 μs (Horiba Fluoromax 4 with TCSPC).

The ΔE(S1–T1)-value of 4a is 1730 cm$^{-1}$ (determined by the energy difference of the fluorescence and phosphorescence band at 298 K and 77 K, respectively).

TABLE 5

Elemental analysis

|  | C | | H | | N | |
|---|---|---|---|---|---|---|
|  | calc.[a] | found | calc.[a] | found | calc.[a] | gef. |
| 10a | 47.89 | 47.73 | 3.76 | 3.62 | 4.75 | 4.55 |

[a]Cu$_2$I$_2$(4-Me-1-TolylImidazolePPh$_2$)$_2$ × 1 molecule CH$_2$Cl$_2$
(calc. = calculated)

Photophysical Characterization

Figure 14:
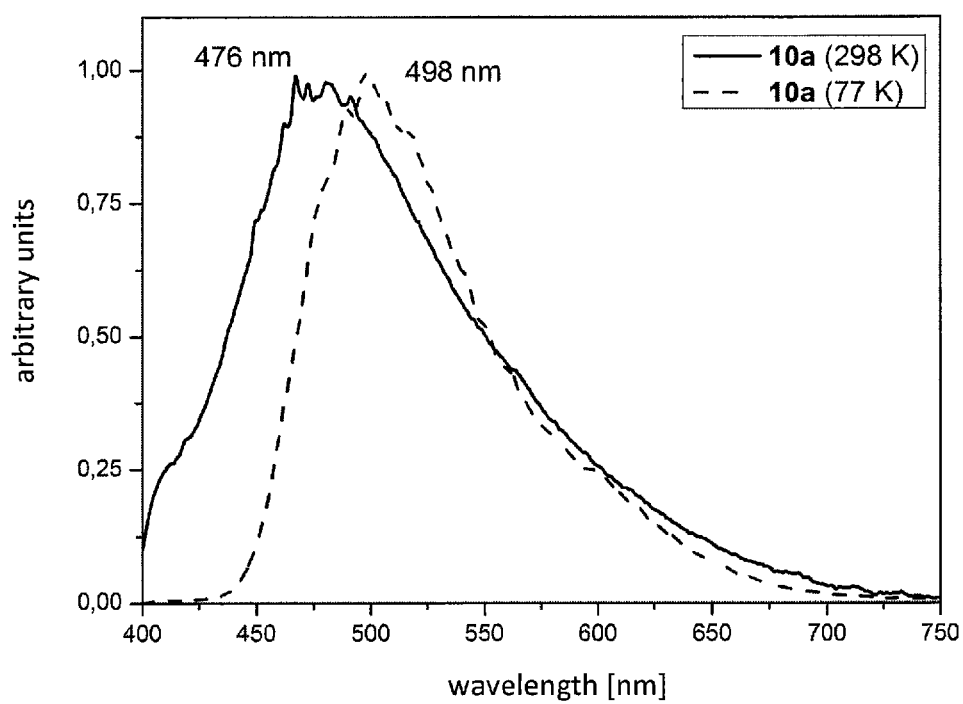
FIG. 14 shows the emission spectra of powder samples of complex 10a in accordance with an embodiment of the present invention.

The emission spectrum of 10a at 298 K is shown in FIG. 14.

The emission spectrum of 10a at 77 K is shown in FIG. 14.

The emission quantum yield of 10a at 298 K is 40% (measured with Hamamatsu C9920-02G)

The emission lifetime of 10a is 9 (Horiba Fluoromax 4 with TCSPC).

The ΔE(S1–T1)-value of 10a is 930 cm$^{-1}$ (determined by the energy difference of the fluorescence and phosphorescence band at 298 K and 77 K, respectively).

VI. P∩N*=QuinolinePPh$_2$, 11: Cu$_2$I$_2$(QuinolinePPh$_2$)$_2$, 12a-c

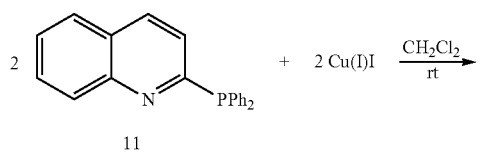

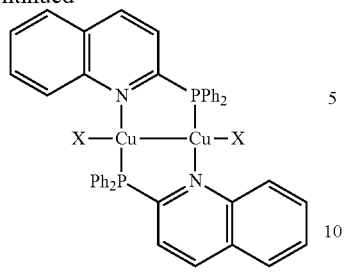

12a: X = I
12b: X = Br
12c: X = Cl

TABLE 6

Elemental analyses

| | C | | H | | N | |
|---|---|---|---|---|---|---|
| | calc. | found | calc. | found | calc. | found |
| 12a | 50.07 | 49.92 | 3.20 | 3.21 | 2.78 | 2.64 |
| 12b[a] | 54.28 | 54.39 | 3.50 | 3.44 | 3.00 | 2.78 |
| 12c[b] | 59.99 | 59.96 | 3.87 | 3.78 | 3.31 | 3.21 |

[a]$Cu_2Br_2(QuinolinePPh_2)_2 \times \frac{1}{4}$ molecule $CH_2Cl_2$
[b]$Cu_2Cl_2(QuinolinePPh_2)_2 \times \frac{1}{4}$ molecule $CH_2Cl_2$
(calc. = calculated)

Photophysical Characterization

Figure 15:
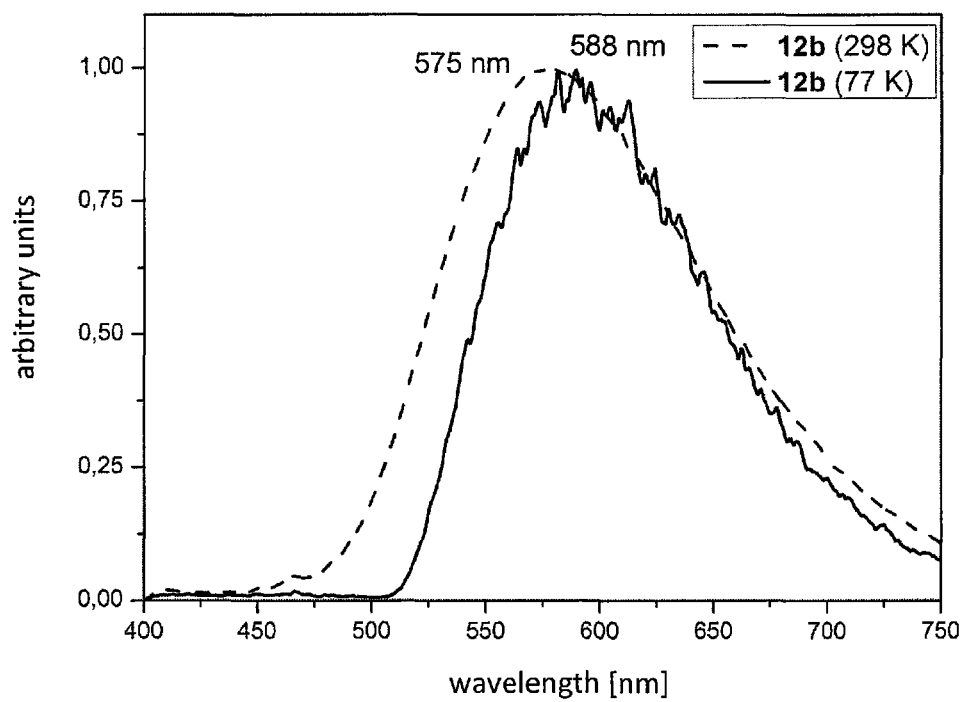
FIG. 15 shows the emission spectra of powder samples of complex 12b in accordance with an embodiment of the present invention.

The emission spectrum of 12b at 298 K is shown in FIG. 15.

The emission spectrum of 12b at 77 K is shown in FIG. 15.

The emission lifetime of 12b is 11 µs (Horiba Fluoromax 4 with TCSPC).

The $\Delta E(S1-T1)$-value of 12b is 380 cm$^{-1}$ (determined by the energy difference of the fluorescence and phosphorescence band at 298 K and 77 K, respectively).

Figure 16:
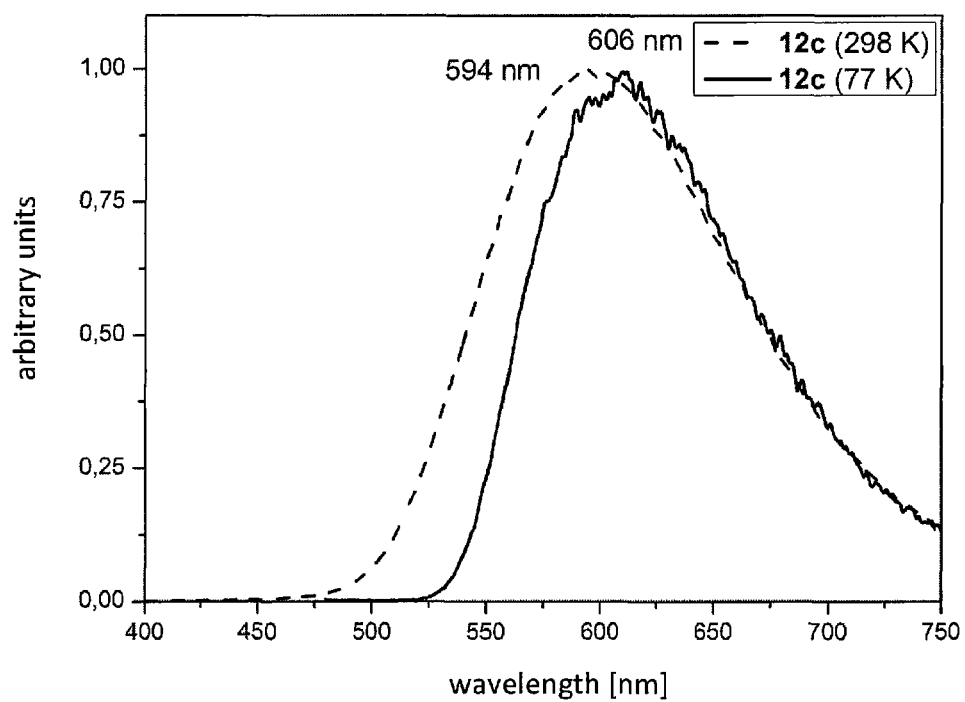
FIG. 16 shows the emission spectra of powder samples of complex 12c in accordance with an embodiment of the present invention.

The emission spectrum of 12c at 298 K is shown in FIG. 16.

The emission spectrum of 12c at 77 K is shown in FIG. 16.

The emission quantum yield of 12c at 298 K is 24% (measured with Hamamatsu C9920-02G)

The emission lifetime of 12c is 16 µs (Horiba Fluoromax 4 with TCSPC).

The $\Delta E(S1-T1)$-value of 12c is 330 cm$^{-1}$ (determined by the energy difference of the fluorescence and phosphorescence band at 298 K and 77 K, respectively).

VII. P∩N*=PhenanthridinePPh$_2$, 13: Cu$_2$I$_2$(PhenanthridinePPh$_2$)$_2$, 14a

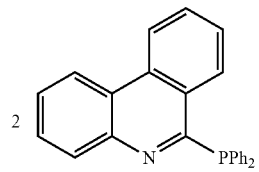

2

+ 2 Cu(I)I $\xrightarrow[\text{rt}]{CH_2Cl_2}$

13

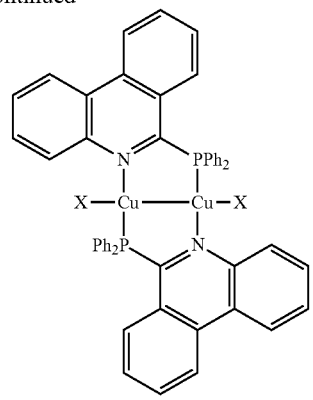

14a: X = I

TABLE 7

Elemental analysis

| | C | | H | | N | |
|---|---|---|---|---|---|---|
| | calc. | found | calc. | found | calc. | found |
| 14a | 54.22 | 54.36 | 3.28 | 3.75 | 2.53 | 4.18 |

(calc. = calculated)

Photophysical Characterization

Figure 17:
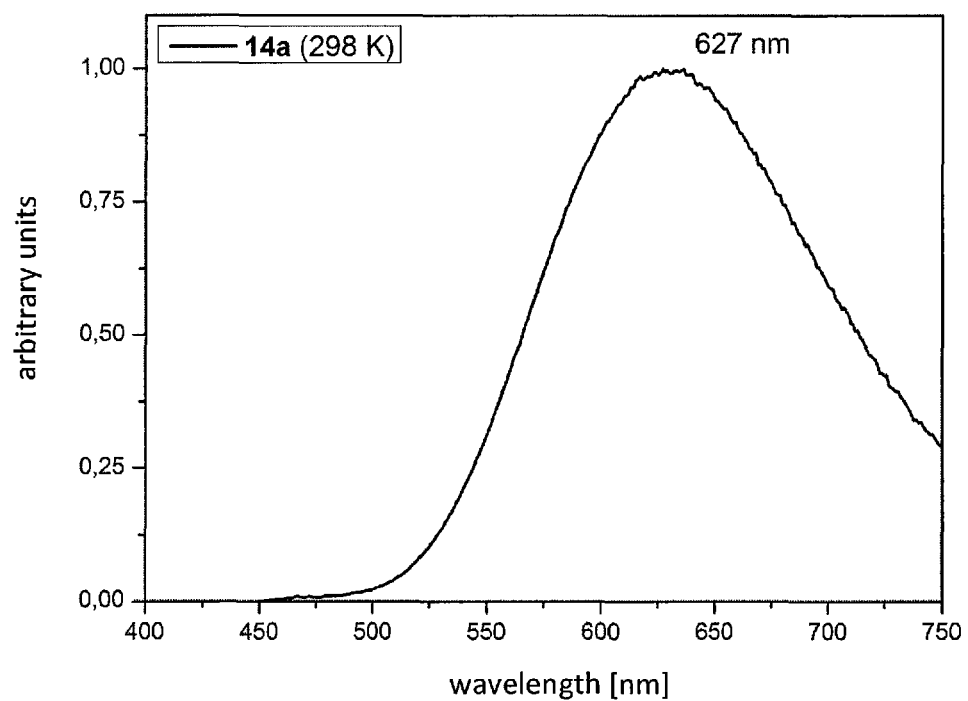
FIG. 17 shows the emission spectra of powder samples of complex 14a in accordance with an embodiment of the present invention.

The emission spectrum of 14a at 298 K is shown in FIG. 17.

The emission lifetime of 14a is 8 µs (Horiba Fluoromax 4 with TCSPC).

VIII. P∩N*=4-Et-QuinazolinePPh$_2$, 15: Cu$_2$I$_2$(4-Et-QuinazolinePPh$_2$)$_2$, 16a

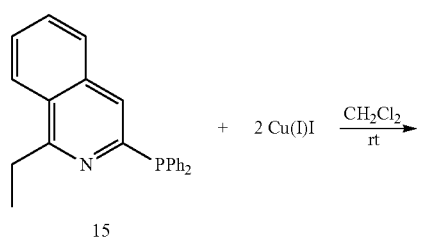

2

+ 2 Cu(I)I $\xrightarrow[\text{rt}]{CH_2Cl_2}$

15

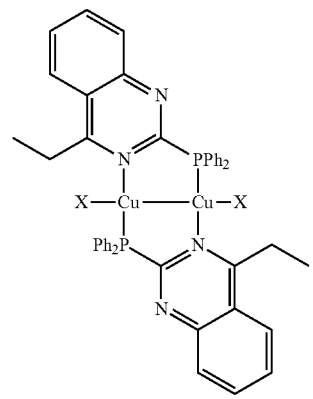

16a: X = I

TABLE 8

| | Elemental analysis | | | | | |
|---|---|---|---|---|---|---|
| | C | | H | | N | |
| | calc. | found | calc. | found | calc. | found |
| 16a | 49.59 | 49.59 | 3.59 | 3.82 | 5.26 | 5.08 |

(calc. = calculated)

Photophysical Characterization

Figure 18:
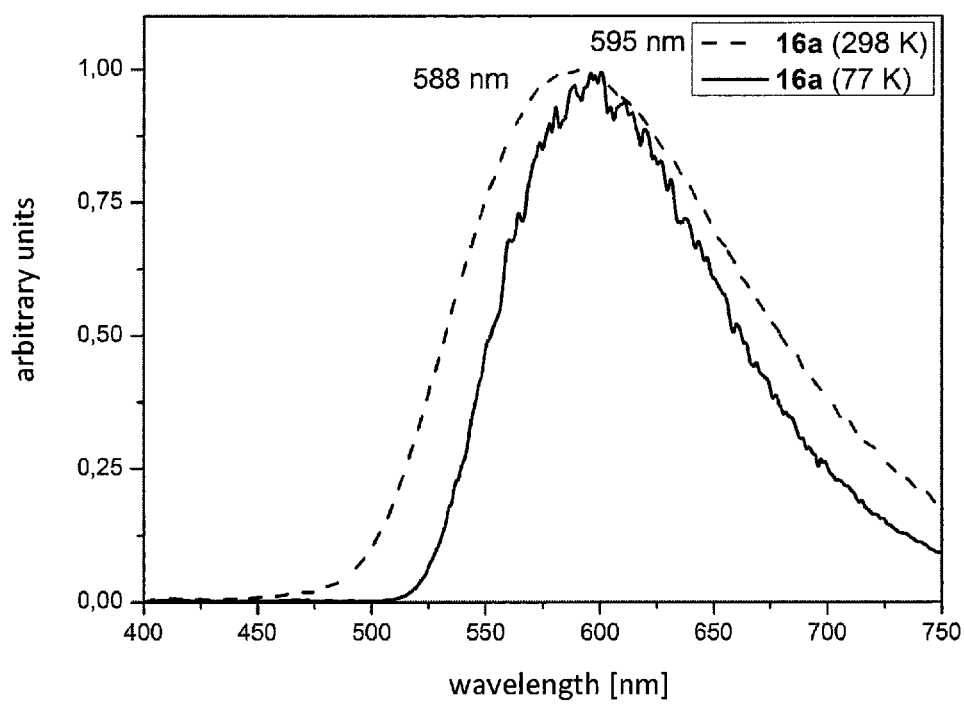
FIG. 18 shows the emission spectra of powder samples of complex 16a in accordance with an embodiment of the present invention.

The emission spectrum of 16a at 298 K is shown in FIG. 18.

The emission spectrum of 16a at 77 K is shown in FIG. 18.

The emission lifetime of 16a is 9 μs (Horiba Fluoromax 4 with TCSPC).

The ΔE(S1–T1)-value of 16a is 200 cm$^{-1}$ (determined by the energy difference of the fluorescence and phosphorescence band at 298 K and 77 K, respectively).

In FIG. 2a, the value of $\tau(T_1)$ in a is an example.

In FIG. 3, the structures result from crystal structure analyses.

In FIG. 4, the dotted curve symbolizes the approximate course of the $S_0$-$S_1$ excitation. The values of the emission quantum yield and the emission decay time measured for T=300 K are also given in the diagram.

In FIG. 5, the parameters specified result from its adaption to the experimental data according to equation 4.

Figure 6:
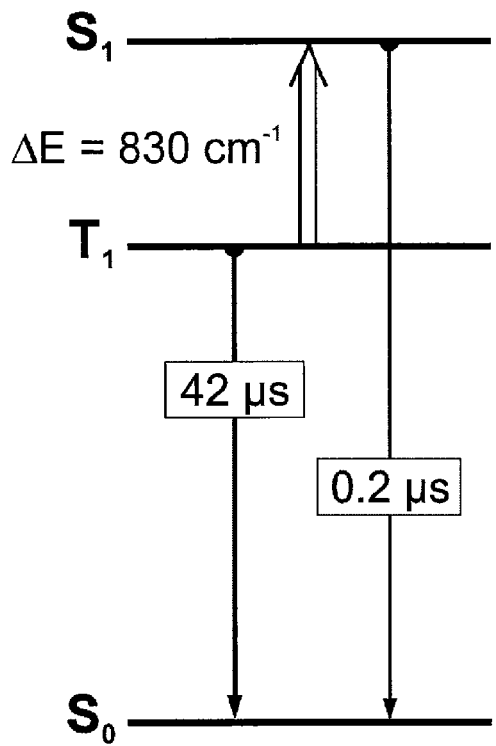
FIG. 6 shows the energy level schemes for the lowest energy levels of Cu$_2$Cl$_2$((6-Me-py)PPh$_2$)$_2$ in accordance with an embodiment of the present invention.

In FIG. 6, the measured decay time $\tau(T_1)$=42 μs given for the $T_1$ state applies for T=77 K, whereas the value of 0.2 μs represents the intrinsic decay time of the fluorescence from the $S_1$ state.

In FIG. 7, the dotted curve symbolizes the approximate course of the $S_0$-$S_1$ excitation. The values of the emission quantum yield and the emission decay time measured for T=300 K are also given in the diagram.

In FIG. 8, the dotted curve symbolizes the approximate course of the $S_0$-$S_1$ excitation. The values of the emission quantum yield and the emission decay time measured for T=300 K are also given in the diagram.

In FIGS. 9-18, the emission spectra of powder samples of complex 4a, 4b, 6a, 6b, 8a, 10a, 12b, 12c, 14a, 16a is shown at T=298 K and T=77 K (excitation at 350 nm each). Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. A copper(I) complex for the emission of light comprising a structure according to formula A:

Formula A $$\begin{array}{c} P \cdots\cdots N \\ | \quad\quad | \\ X-Cu-Cu-X \\ | \quad\quad | \\ N \cdots\cdots P \end{array}$$

wherein:

Cu is Cu(I);

X is selected from the group consisting of Cl, Br, I, SCN, CN, and alkynyl (R*—≡), wherein R*=R;

P∩N is a phosphine ligand substituted with an N-heterocycle comprising a structure according to formula B:

Formula B $$R \underset{E'}{\overset{\gamma}{\diagdown}} \underset{\beta}{\overset{N}{\diagdown}} \underset{E}{\overset{\alpha}{\diagdown}} P - R''$$
$$\phantom{xxxxxxx} | $$
$$\phantom{xxxxxxx} R'$$

wherein:

E is a carbon or a nitrogen atom;

E' is a carbon or nitrogen atom, not substituted with a hydrogen atom;

dotted bond represents a single or double bond;

R is selected from the group consisting of a substituted or unsubstituted alkyl group [$CH_3$—$(CH_2)_n$-] (n is an integer from 0 to 20), a substituted or unsubstituted aryl group, and an unsaturated group selected from an alkenyl and an alkynyl group, wherein R is not a hydrogen atom;

R', R" are independently selected from the group consisting of a substituted or unsubstituted alkyl group [$CH_3$—$(CH_2)_n$-] (n is an integer from 0 to 20), a substituted or unsubstituted aryl group, and a heteroaryl group, wherein R' and R" are each directly bound to the phosphorous atom of the phosphine ligand; and wherein the N-heterocycle is an aromatic 6- or 5-membered ring selected from:

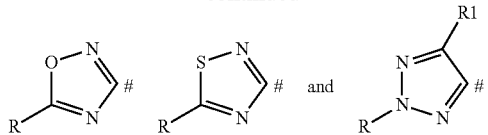

wherein
R1, R2, R3, are each selected from the group consisting of hydrogen, a substituted or unsubstituted alkyl group [$CH_3-(CH_2)_n$] (n is an integer from 0 to 20), a substituted or unsubstituted aryl group, and an unsaturated group selected from an alkenyl and an alkynyl group; and
wherein the N-heterocycle is linked to the phosphorous atom at the positions marked with #.

2. The copper(I) complex of claim 1, wherein R is an alkyl group [$CH_3-(CH_2)_n$-] (n is an integer from 0 to 20) substituted with halogens.

3. The copper(I) complex of claim 1, wherein R is an aryl group substituted with an alkyl group, a halogen, a silane (—$SiR^*_3$) wherein R* is the same as R1, or an ether group —OR wherein R is the same as R1.

4. The copper(I) complex of claim 1, wherein R is an unsaturated group substituted with an alkyl group, a halogen, a silane (—$SiR^*_3$) wherein R* is the same as R1, or an ether group —OR wherein R is the same as R1.

5. The copper(I) complex of claim 1, wherein R' and R" are independently an alkyl group [$CH_3-(CH_2)_n$-] with n is an integer >6.

6. The copper(I) complex of claim 1, wherein the aryl and heteroaryl groups are substituted with alkyl groups, halogens, silane (—$SiR^*_3$) or ether groups —OR*, wherein R* is the same as R1.

7. The copper(I) complex of claim 1, wherein R1, R2, and R3 are hydrogen atoms.

8. The copper(I) complex of claim 1, wherein R, R1, R2, and R3 form annulated ring systems.

9. The copper(I) complex of claim 1, wherein R, R1, R2, R3, R' and R" increase the solubility of the copper(I) complex in organic solvents.

10. The copper(I) complex of claim 1 further comprising:
a $\Delta E(S_1-T_1)$-value between a lowest triplet state and a singlet state above the lowest triplet state of less than 2500 $cm^{-1}$;
an emission quantum yield of greater than 20%; and
an emission lifetime of at most 20 μs.

11. The copper(I) complex of claim 1, wherein the copper(I) complex is used for emission of light in an emitter layer in an optoelectronic device.

12. A method for manufacturing an optoelectronic device using the copper(I) complex of claim 1, wherein the copper(I) complex is applied to a solid by using a wet-chemical process, a colloidal suspension process, or a sublimation process.

13. The method according to claim 12, wherein the manufacturing is performed by using a wet-chemical process comprising:
depositing a first copper(I) complex that is dissolved in a first solvent onto a carrier; and
depositing a second copper(I) complex that is dissolved in a second solvent onto the carrier;
wherein the first copper(I) complex is not soluble in the second solvent and the second copper(I) complex is not soluble in the first solvent;
wherein the first copper(I) complex and the second copper(I) complex are each a copper(I) complex according to claim 1.

14. The method of claim 13 further comprising:
depositing a third copper(I) complex that is dissolved in the first solvent or in a third solvent onto the carrier;
wherein the third copper(I) complex is a copper(I) complex according to claim 1.

15. The method according to claim 14, wherein the optoelectronic device is a white light-OLED, wherein the first copper(I) complex is a red light emitter, the second copper(I) complex is a green light emitter and the third copper(I) complex is a blue light emitter.

16. An optoelectronic device, comprising a copper(I) complex comprising a ΔE difference between a lowest triplet state and a singlet state above the lowest triplet state between 50 $cm^{-1}$ and 2500 $cm^{-1}$.

17. The optoelectronic device of claim 16, wherein the copper(I) complex is a copper(I) complex according to claim 1 used for emission of light in an emitter layer in the optoelectronic device.

18. The optoelectronic device of claim 17, wherein a fraction of the copper(I) complex in the emitter layer is in the range of 2% to 100% by weight with respect to a total weight of the emitter layer.

19. The optoelectronic device of claim 18, wherein the optoelectronic device is an organic light emitting diode (OLED).

20. The optoelectronic device of claim 17, wherein the optoelectronic device is selected from the group consisting of an organic light emitting diode (OLED), a light-emitting electrochemical cell, an OLED-sensor, a gas or a vapor sensor that is not hermetically sealed from the outside, an optical temperature sensor, an organic solar cell (OSC), an organic field-effect transistor, an organic laser, an organic diode, an organic photo diode and a down conversion system.

* * * * *